United States Patent
Han et al.

(10) Patent No.: US 12,347,633 B2
(45) Date of Patent: Jul. 1, 2025

(54) TO-BE-DETECTED IMPLEMENT FOR REHABILITATION TRAINING AND REHABILITATION TRAINING SYSTEM

(71) Applicant: MORETHINGS CO., LTD., Yongin-si (KR)

(72) Inventors: Jeong Min Han, Seoul (KR); Jae Kyung Kwak, Yongin-si (KR); Ji Won Oh, Gwangju-si (KR); Hwan Il Park, Seoul (KR); Kwang Dek An, Hwaseong-si (KR)

(73) Assignee: MORETHINGS CO., LTD., Yongin-si (KR)

( * ) Notice: Subject to any disclaimer, the term of this patent is extended or adjusted under 35 U.S.C. 154(b) by 760 days.

(21) Appl. No.: 17/507,882

(22) Filed: Oct. 22, 2021

(65) Prior Publication Data
US 2022/0044890 A1  Feb. 10, 2022

Related U.S. Application Data

(63) Continuation of application No. PCT/KR2019/008128, filed on Jul. 3, 2019.

(30) Foreign Application Priority Data

Apr. 22, 2019  (KR) .................. 10-2019-0046730

(51) Int. Cl.
*H01H 25/06* (2006.01)
*A61B 5/11* (2006.01)
(Continued)

(52) U.S. Cl.
CPC .......... *H01H 25/06* (2013.01); *A61B 5/1124* (2013.01); *A61B 5/1126* (2013.01); *A63B 23/12* (2013.01);
(Continued)

(58) Field of Classification Search
CPC ................................ H01H 1/5805; G09B 5/00
See application file for complete search history.

(56) References Cited

U.S. PATENT DOCUMENTS

| 6,443,796 B1 | 9/2002 | Shackelford |
| 8,992,229 B2 * | 3/2015 | Spital .................. A63F 9/00 434/259 |

(Continued)

FOREIGN PATENT DOCUMENTS

| JP | 2004-209060 A | 7/2004 |
| JP | 2004-267406 A | 9/2004 |

(Continued)

OTHER PUBLICATIONS

The extended European search report issued by the European Patent Office on Oct. 28, 2022, which corresponds to European Patent Application No. 19926503.4-1122 and is related to U.S. Appl. No. 17/507,882.

*Primary Examiner* — Jay Trent Liddle
*Assistant Examiner* — Alyssa N Brandley
(74) *Attorney, Agent, or Firm* — Studebaker Brackett PLLC

(57) ABSTRACT

Provided are a to-be-detected implement for rehabilitation training and a rehabilitation training system. The to-be-detected implement for rehabilitation training comprises: a cylinder-shaped main body with an opening in at least one side thereof; a first electrode portion formed on one region of the circumference of the main body; a second electrode portion separated from the first electrode portion and formed on another region of the circumference of the main body; and a guide portion which is formed between the first electrode portion and the second electrode portion to block the electrical connection between the first electrode portion and the second electrode portion, and which is recessed or (Continued)

protrudes at the circumference of the main body to a predetermined depth.

15 Claims, 19 Drawing Sheets

(51) Int. Cl.
    *A63B 23/12*     (2006.01)
    *G09B 5/00*     (2006.01)
    *G09B 19/00*     (2006.01)
    *H01H 1/58*     (2006.01)

(52) U.S. Cl.
    CPC ............ *G09B 5/00* (2013.01); *G09B 19/003* (2013.01); *H01H 1/5805* (2013.01); *A61B 2505/09* (2013.01)

(56) References Cited

U.S. PATENT DOCUMENTS

| | | | |
|---|---|---|---|
| 10,112,107 B2 * | 10/2018 | Hirai | A63F 9/24 |
| 11,521,508 B2 * | 12/2022 | Roh | G09B 1/38 |
| 2008/0113319 A1 * | 5/2008 | Davis | G09B 1/02 |
| | | | 434/128 |
| 2018/0085624 A1 * | 3/2018 | Choi | A61H 1/02 |
| 2018/0133591 A1 * | 5/2018 | Hirai | G09B 19/22 |
| 2020/0269128 A1 * | 8/2020 | Yang | G09B 1/36 |

FOREIGN PATENT DOCUMENTS

| | | | | |
|---|---|---|---|---|
| JP | 2010054372 A | * | 3/2010 | |
| JP | 2018-033692 A | | 3/2018 | |
| KR | 10-2014-0019566 A | | 2/2014 | |
| KR | 10-1708407 B1 | | 2/2017 | |
| KR | 1708407 B1 | * | 2/2017 | ........... A63H 33/042 |
| KR | 10-2019-0008410 A | | 1/2019 | |

* cited by examiner

TO-BE-DETECTED IMPLEMENT FOR REHABILITATION TRAINING AND REHABILITATION TRAINING SYSTEM

TECHNICAL FIELD

The present invention relates to a to-be-detected implement for rehabilitation training and a rehabilitation training system.

BACKGROUND ART

According to the statistic by Korean Employment Agency for Persons with Disabilities in 2018, the number of people with disabilities registered in Korean accounts for 4.8% of the whole population, in which physical disabilities was found as 52.9% which is the highest ratio. In such disabilities, disabilities of arms due to disabilities of the central nervous system such as cerebral apoplexy are the most common physical disabilities.

The function of arms is a function closely connected with daily life such as eating food, holding objects, turning a door knob, and writing with hands. When there is a disability of arms, large inconvenience is caused in daily life, so there is a need for a rehabilitation training apparatus for overcoming a disability of arms.

However, rehabilitation training apparatuses developed up to now for disabilities of arms are wearing apparatuses such as a glove type or a band type rather than an apparatus for easily enabling objects, so there is limitation in direct experience of senses such as the sense of touch and proprioception that are recognized through the fingers of a user.

Further, rehabilitation training is performed by therapists and analogue training tools at the sites of rehabilitation training for disabilities of arms and therapists have different standards for determining the rehabilitation training results, so uniform rehabilitation training is difficult.

Accordingly, it is required to develop an apparatus that can provide effective rehabilitation training for disabilities of arms.

PRIOR ART DOCUMENT

Patent Document

Korean Patent No. 10-1855359, 2018.04.30.

DISCLOSURE

Technical Problem

An objective of the present invention is to provide a to-be-detected implement for rehabilitation training and a rehabilitation training system.

The objectives of the present invention are not limited to the objects described above and other objectives will be clearly understood by those skilled in the art from the following description.

Technical Solution

A to-be-detected implement for rehabilitation training according to an embodiment of the present invention for achieving the objectives includes: a body having a cylindrical shape with at least one open side; a first electrode formed in a region of the circumference of the body; a second electrode spaced apart from the first electrode and formed in another region of the circumference of the body; and a guide formed blocking electrical connection of the first electrode and the second electrode by being formed between the first electrode and the second electrode, and recessed or protruded a predetermined depth on the circumference of the body.

In an embodiment, the to-be-detected implement further includes a to-be-detected part being in contact with the first electrode on a side and the second electrode on another side, and configured as a resistor having a predetermined resistance value or a capacitor having a predetermined capacitance value.

The body has a predetermined gradient, and when one to-be-detected implement is stacked over another to-be-detected implement, the guides of the two to-be-detected implements are fitted to each other.

A rehabilitation training system according to an embodiment of the present invention for achieving the objectives includes: a to-be-detected implement; and a control board including a plurality of sockets that correspond to the shape of the bottom of the to-be-detected implement and in which the to-be-detected implement is inserted, wherein the socket includes: a third electrode formed in a region of the lower portion of each of the plurality of sockets; and a fourth electrode spaced apart from the third electrode and formed in another region of the lower portion of each of the plurality of sockets, and the control board includes: an insertion detector electrically connected to each of the third electrode and the fourth electrode and detecting an electrical change due to insertion of the to-be-detected implement; and a controller determining the position of the socket in which the to-be-detected implement is inserted on the basis of the detected electrical change.

In an embodiment, the body has a predetermined gradient, and when a to-be-detected implement is inserted in the socket of the control board and another to-be-detected implement is additionally stacked over the to-be-detected implement inserted in the control board, the guides of the two to-be-detected implements are fitted to each other, so the two to-be-detected implements are electrically connected to each other.

In an embodiment, as the two to-be-detected implements are electrically connected to each other, the insertion detector calculates the number of the stacked to-be-detected implements by detecting a change due to parallel connection of resistors or capacitors of the to-be-detected parts, and the controller determines the position of the socket in which the to-be-detected implements are additionally inserted on the basis of a change of resistors or capacitors due to the parallel connection.

In an embodiment, the to-be-detected implement is provided as a plurality of pieces, the plurality of to-be-detected implements are classified into a plurality of to-be-detected implement groups, and the to-be-detected parts have different values of resistors or capacitors in the plurality of to-be-detected implement groups.

In an embodiment, the control board further includes a controller generating insertion information of the position or order of a socket in which the to-be-detected implement should be inserted of the plurality of sockets of the control board on by a predetermined reference.

In an embodiment, the socket further includes a light emitter disposed to correspond to the position of each of the plurality of sockets and emitting light on the basis of the insertion information.

A to-be-detected implement for rehabilitation training according to another embodiment of the present invention for achieving the objectives includes: a body having a cylindrical shape with at least one open side; a first electrode formed in a region of the circumference of the body; a second electrode spaced apart from the first electrode and formed in another region of the circumference of the body; and a guide formed blocking electrical connection of the first electrode and the second electrode by being formed between the first electrode and the second electrode, recessed or protruded a predetermined depth on the circumference of the to-be-detected implement, and biased to a side of the circumference of the to-be-detected implement.

In an embodiment, the to-be-detected implement further includes a to-be-detected part being in contact with the first electrode on a side and the second electrode on another side, and configured as a first coil having a predetermined inductance value.

The body has a predetermined gradient, and when one to-be-detected implement is stacked over another to-be-detected implement, the guides of the two to-be-detected implements are fitted to each other.

A rehabilitation training system according to another embodiment of the present invention for achieving the objectives includes: a to-be-detected implement; and a control board including a plurality of sockets that correspond to the shape of the bottom of the to-be-detected implement and in which the to-be-detected implement is inserted, wherein the socket includes: a third electrode formed in a region of the lower portion of each of the plurality of sockets; and a fourth electrode spaced apart from the third electrode and formed in another region of the lower portion of each of the plurality of sockets, and the control board includes: a magnetic field generator disposed at the lower portion of each of the plurality of sockets; an insertion detector electrically connected to each of the third electrode and the fourth electrode and detecting an electrical change due to insertion of the to-be-detected implement; and a controller determining the position of the socket in which the to-be-detected implement is inserted on the basis of the detected electrical change.

In an embodiment, the body has a predetermined gradient, and when a to-be-detected implement is inserted in the socket of the control board and another to-be-detected implement is additionally stacked over the to-be-detected implement inserted in the control board, the guides of the two to-be-detected implements are fitted to each other, so the two to-be-detected implements are electrically connected to each other.

In an embodiment, as the two to-be-detected implements are electrically connected to each other, the insertion detector calculates the number of the stacked to-be-detected implements by detecting a change of an induced current due to parallel connection of first coils of the to-be-detected parts, and the controller determines the position of the socket in which the to-be-detected implements are additionally inserted on the basis of a change of an induced current due to the parallel connection.

In an embodiment, the to-be-detected implement is provided as a plurality of pieces, the plurality of to-be-detected implements are classified into a plurality of to-be-detected implement groups, and the inductance values of the first coils of the to-be-detected parts are different in the plurality of to-be-detected implement groups.

In an embodiment, the control board further includes a controller generating insertion information of the position or order of a socket in which the to-be-detected implement should be inserted of the plurality of sockets of the control board on by a predetermined reference.

In an embodiment, the socket further includes a light emitter disposed to correspond to the position of each of the plurality of sockets and emitting light on the basis of the insertion information.

The other details of the present invention are included in the following detailed description and the accompanying drawings.

Advantageous Effects

According to the to-be-detected implement for rehabilitation training and the rehabilitation training system of the present invention, two to-be-detected implements are stacked and coupled to each other by the guides of the to-be-detected implements, so they can be electrically connected.

Further, the control board detects insertion of a to-be-detected implement, thereby being able to manage data of the result of rehabilitation training such as the accuracy of insertion and the taken time such as collecting, storing, and analyzing the data.

Further, by the control board, it is possible to output a uniform result of rehabilitation training excluding subjective determination of a rehabilitation training therapist.

Further, the control board can provide user-customized rehabilitation training to the user by managing rehabilitation training data of the user.

The effects of the present invention are not limited to those described above and other effects may be made apparent to those skilled in the art from claims.

BEST MODE

Figure 1:
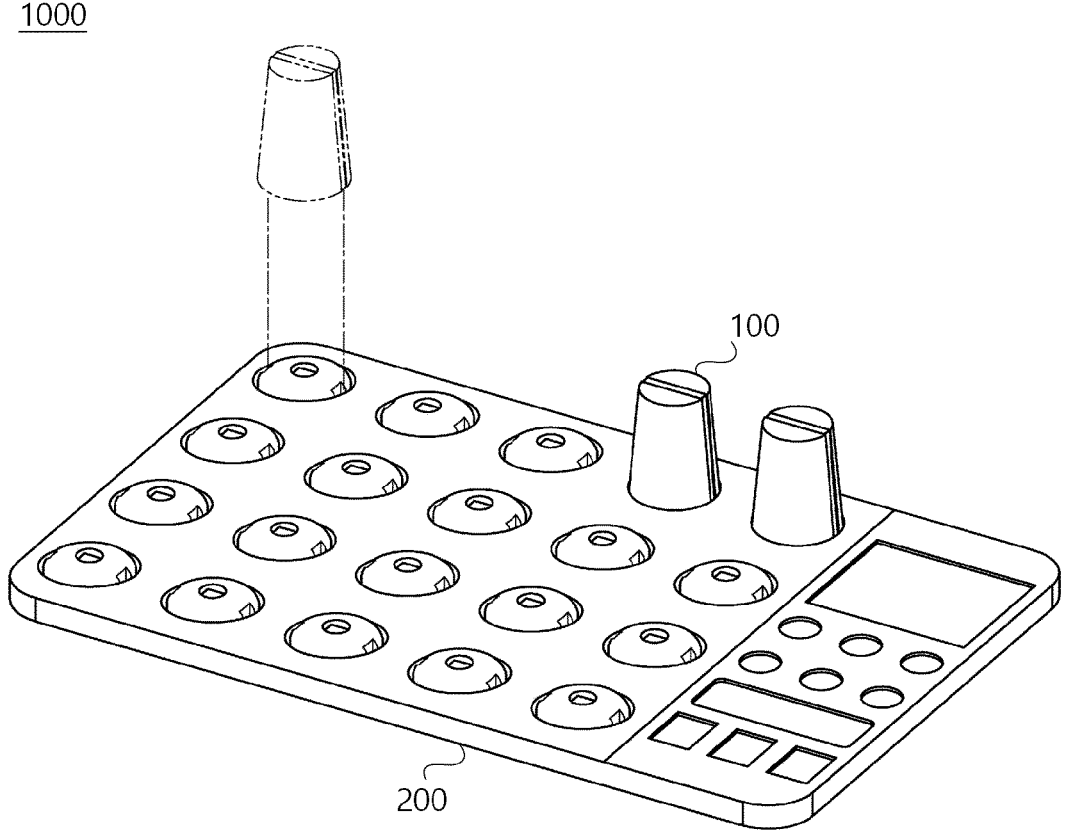
FIG. 1 is a conceptual view of a rehabilitation training system including a to-be-detected implement for rehabilitation training and a control board.

The advantages and features of the present invention, and methods of achieving them will be clear by referring to the exemplary embodiments that will be describe hereafter in detail with reference to the accompanying drawings. However, the present invention is not limited to the exemplary embodiments described hereafter and may be implemented in various ways, and the exemplary embodiments are provided to complete the description of the present invention and let those skilled in the art completely know the scope of the present invention and the present invention is defined by claims.

The terms used herein are provided to describe embodiments without limiting the present invention. In the specification, a singular form includes a plural form unless specifically stated in the sentences. The terms "comprise" and/or "comprising" used herein do not exclude that another component exists or is added other than the stated component. Throughout the specification, the same reference numerals indicate the same components, and the term "and/or" includes each of the stated components and all of one or more combinations. Although the terms 'first', 'second', etc. are used to describe various components, it should be noted that these components are not limited by the terms. These terms are used only for discriminating a component from another component. Accordingly, it should be noted that a first component that is stated below may be a second component within the spirit of the present invention.

Unless defined otherwise, all terms (including technological and scientific terminologies) used herein may be used as meanings that those skilled in the art can commonly understand. Terms defined in common dictionaries are not construed ideally or excessively unless specifically clearly defined.

Spatial relative terms "below", "beneath", "lower", "above", "upper", etc. may be used to easily describe the correlation of one component and another component, as shown in the drawings. The spatially relative terms should be construed as terminologies including different directions of components in using or in operating in addition to the directions shown in drawings. For example, when components shown in the drawings are turned upside down, a component described as being "below" or "beneath" another component may be positioned "above" the another component. Accordingly, "below" and "beneath" that are exemplary terms may include both of up and down directions. A component may be oriented in different directions, so the spatially relative terms may be construed in accordance with orientation.

Hereinafter, embodiments of the present invention will be described in detail with reference to the accompanying drawings.

FIG. 1 is a conceptual view of a rehabilitation training system including a to-be-detected implement for rehabilitation training and a control board.

Referring to FIG. 1, a rehabilitation training system 1000 includes a to-be-detected implement 100 and a control board.

A user of the rehabilitation training system 1000 checks instructions output from the control board 200 (light by a light emitter, audio by an audio interface, or the like), and inserts the to-be-detected implements 100 in sockets of the control board 200. When a to-be-detected implement 100 is inserted in the control board 200, the control board 200 can output feedback (light by a light emitter, audio by an audio interface, or the like) on the basis of the accuracy of the position of the socket in which the to-be-detected implement 100 is inserted, and the taken time. Further, the control board 200 can output a training grade using a display or an audio interface by calculating the training grade of a user on the basis of the accuracy of the position of the socket in which the to-be-detected implement 100 is inserted, and the taken time. The user can perform rehabilitation training and can be provided with the performance result using the rehabilitation training system 1000 even without a rehabilitation training therapist.

The rehabilitation training system 1000 can manage the rehabilitation training data of the user and can provide user-customized rehabilitation training to the user on the basis of the rehabilitation training data. For example, when a user determines that a physical disability is improved while performing rehabilitation training, the rehabilitation training system 1000 can adjust the difficulty of the rehabilitation training in accordance with the degree of the physical disability of the user.

Figure 2:
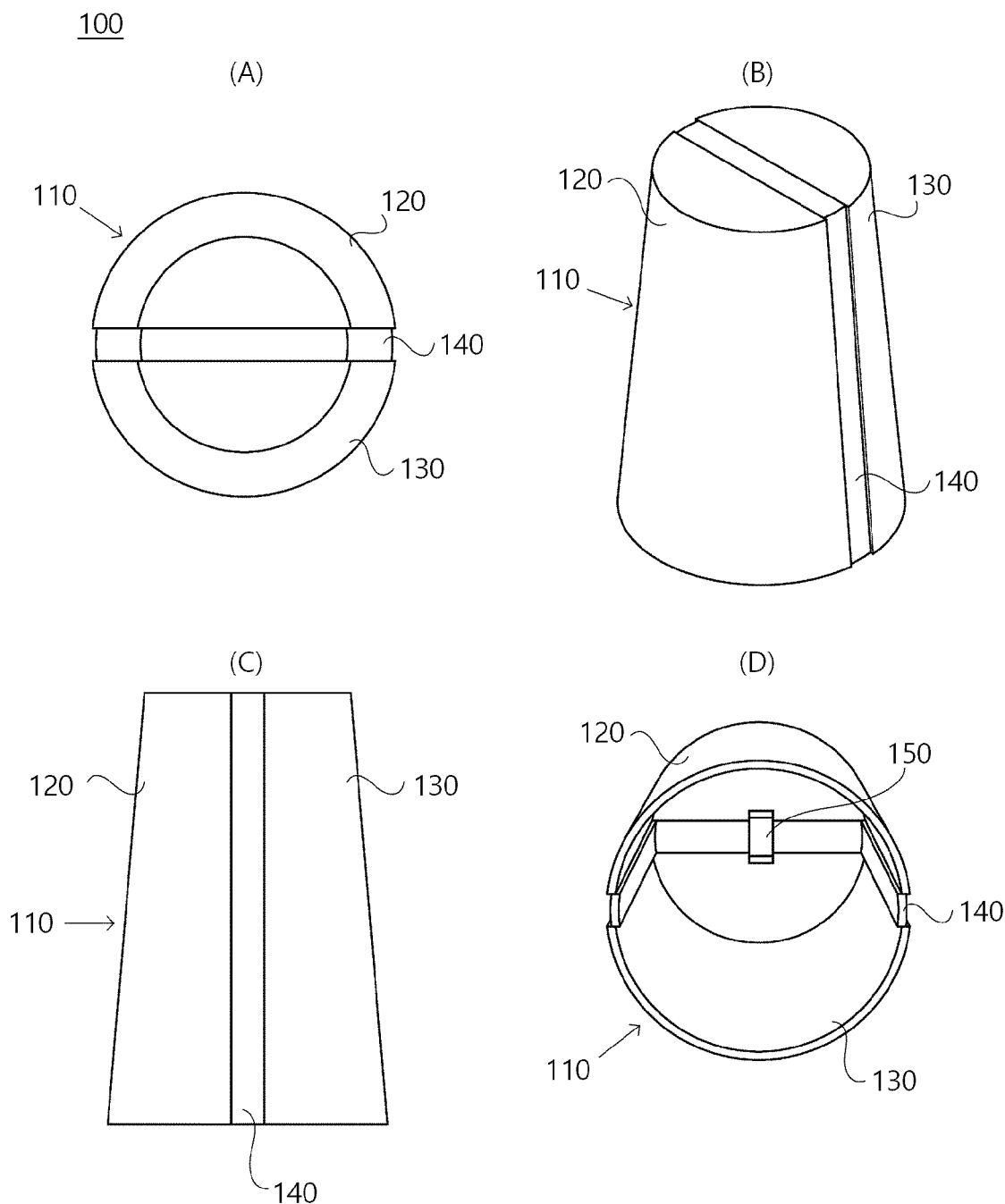
FIG. 2 is a perspective view, a plan view, and a side view of a to-be-detected implement for rehabilitation training according to an embodiment of the present invention.

FIG. 2 is a perspective view and a side view of a to-be-detected implement for rehabilitation training according to an embodiment of the present invention.

Referring to FIG. 2, the to-be-detected implement 100 includes a body 110, a first electrode 120, a second electrode 130, a guide 140, and a to-be-detected part 150. The top of the to-be-detected implement 100 is shown in FIG. 2A, the side of the to-be-detected implement 100 is shown in FIGS. 2B and 2C, and the bottom of the to-be-detected implement 100 is shown in FIG. 2D.

The body 110 of the to-be-detected implement 100 has a cylindrical shape of which at least one side is open. The shape of the body 110 of the to-be-detected implement 100 may be open on one side or open on two sides. Further, the shape of the body 110 of the to-be-detected implement 100 may be a cylindrical, conical, or frustoconical shape, but is not limited thereto. A to-be-detected implement 100 having a frustoconical shape of which one side is open is shown in FIG. 2. Further, the shape of the bottom of the to-be-detected implement 100 may be a circle, an ellipse, a triangle, or a rectangle, but is not limited thereto.

The first electrode 120 of the to-be-detected implement 100 is formed in a partial region of the circumference of the body 110. The first electrode 120 is formed in a partial region of the outer surface, the inner surface, and the bottom of the body 110. The first electrode 120 may be formed on the top of the body 110 or may not be formed on the top of the body 110. The first electrode 120 is made of a conductive material.

The second electrode 130 of the to-be-detected implement 100 is spaced apart from the first electrode 120 and is formed in another partial region of the circumference of the body 110. The second electrode 130 is formed in a partial region of the outer surface, the inner surface, and the bottom of the body 110. The second electrode 130 may be formed on the top of the body 110 or may not be formed on the top of the body 110. The second electrode 130 is made of a conductive material.

The guide 140 of the to-be-detected implement 100 is formed between the first electrode 120 and the second electrode 130. The guide 140 may be formed in the middle regions of the side and the top of the body 110 of the to-be-detected implement 100 may be formed biasedly to a side.

Further, the guide 140 blocks electrical connection between the first electrode 120 and the second electrode 130. The guide 140 is made of a non-conductive material, unlike the first electrode 120 and the second electrode 130.

Further, the guide 140 may be recessed a predetermined depth or may protrude on the circumference of the body 110. The recessed or protruding guide 140 may be a reference for the direction of insertion in the control board 200 to be described below. Further, when two to-be-detected implements 100 are stacked, the recessed or protruding guide 140 may be a reference of the stacking direction. Depending on cases, the guide 140 may not be recessed or protruded and a recessed or protruding region may be formed on at least one of the first electrode 120 and the second electrode 130.

The to-be-detected part 150 of the to-be-detected implement 100 is in contact with the first electrode 120 on a side and the second electrode 130 on another side. The to-be-detected part 150 is configured as a resistor having a predetermined resistance value or a capacitor having a predetermined capacitance value. The to-be-detected implement 100 becomes a unit having a predetermined electrical characteristic by the to-be-detected implement 150.

Figure 3:
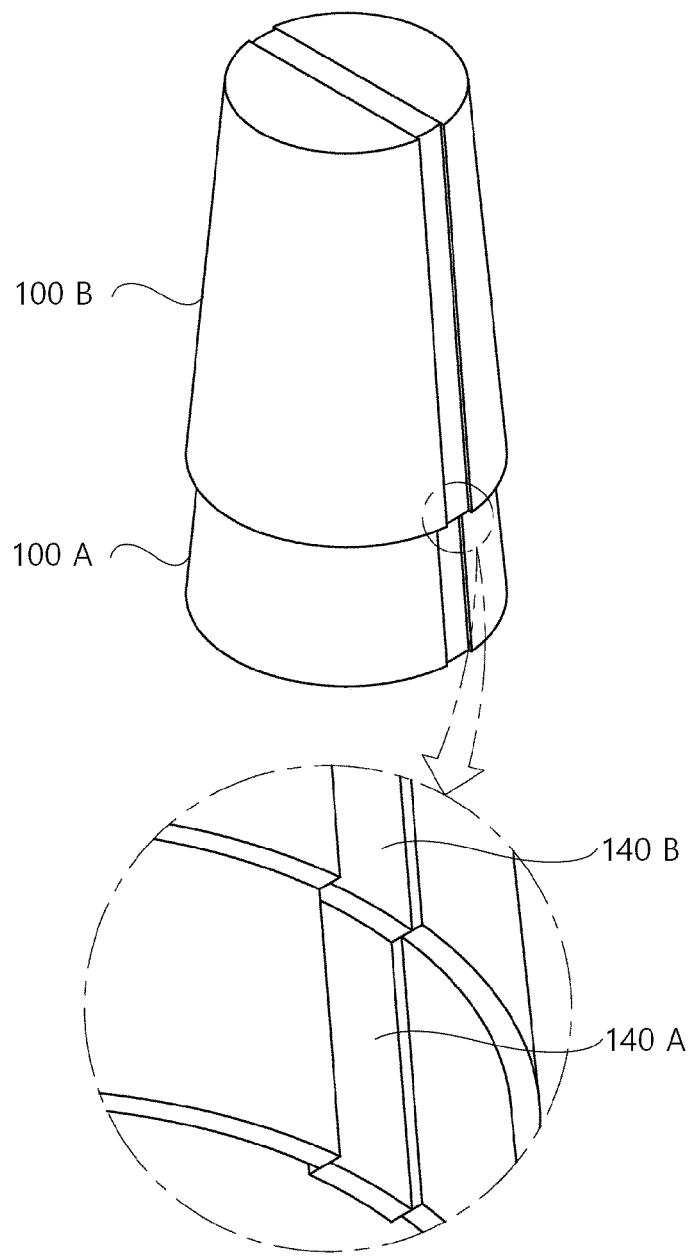
FIG. 3 is a perspective view in which to-be-detected implements for rehabilitation training of FIG. 2 are stacked.

FIG. 3 is a perspective view in which to-be-detected implements for rehabilitation training of FIG. 2 are stacked.

Referring to FIG. 3, one to-be-detected implement 100 B is stacked over another to-be-detected implement 100 A.

The body 110 of the to-be-detected implement 100 may have a predetermined gradient. Two or more to-be-detected implements 100 of which the shapes of the bodies 110 have a predetermined gradient may be piled and stacked up. When one to-be-detected 100 B is stacked over another to-be-detected implement 100 A, the guide 140B of one to-be-detected implement 100 B is fitted to the guide 140 A of another to-be-detected implement 100 A. That is, the inner side of the recessed or protruding region of the guide 140 B of one to-be-detected implement 100 B is fitted to the outer surface of the recessed or protruding region of the guide 140 A of another to-be-detected implement 100 A.

When two or more to-be-detected implements 100 are stacked, the to-be-detected parts 150 of the two or more to-be-detected implements 100 are connected in parallel. Accordingly, when the to-be-detected part 150 is configured as a resistor having a predetermined resistance value, the to-be-detected parts 150 are connected in parallel and the entire resistance value decreases when two or more to-be-detected implements 100 are stacked. Further, when the to-be-detected part 150 is configured as a capacitor having a predetermined capacitance value, the to-be-detected parts 150 are connected in parallel and the entire capacitance value increases when two or more to-be-detected implements 100 are stacked.

Figure 4:
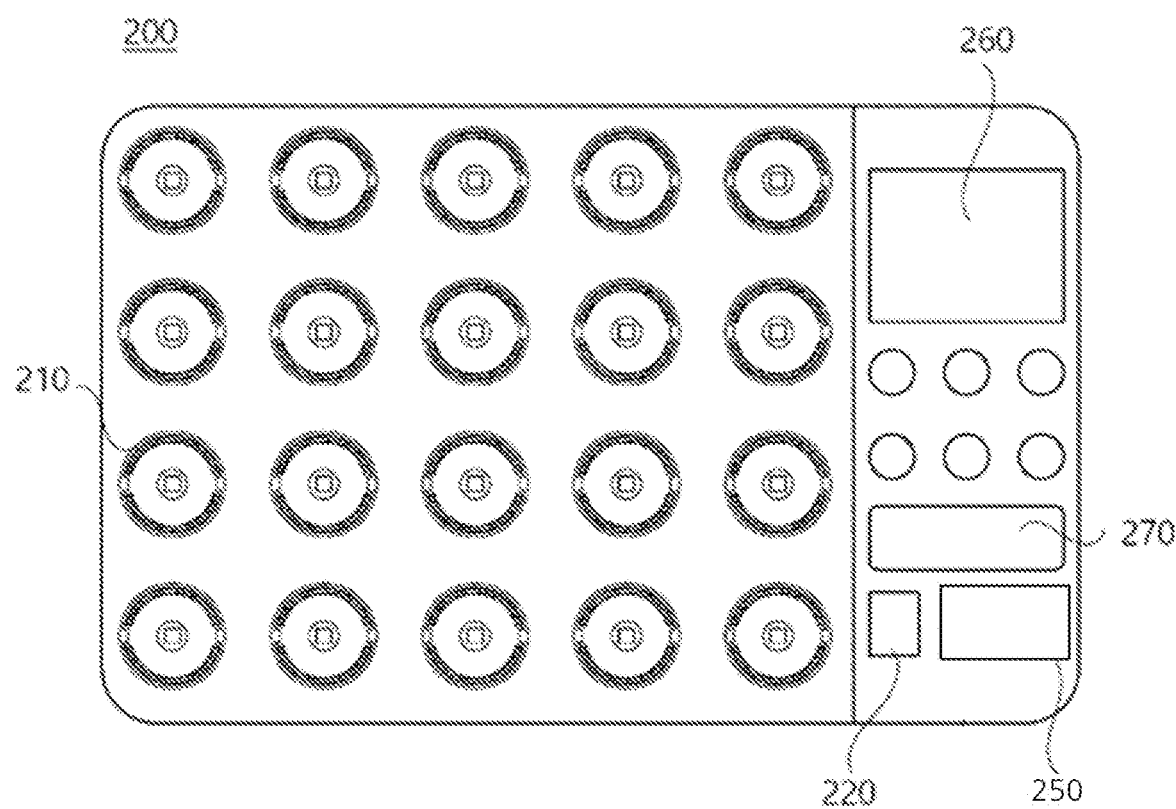
FIG. 4 is a plan view of a control board according to an embodiment of the present invention.
Figure 5:
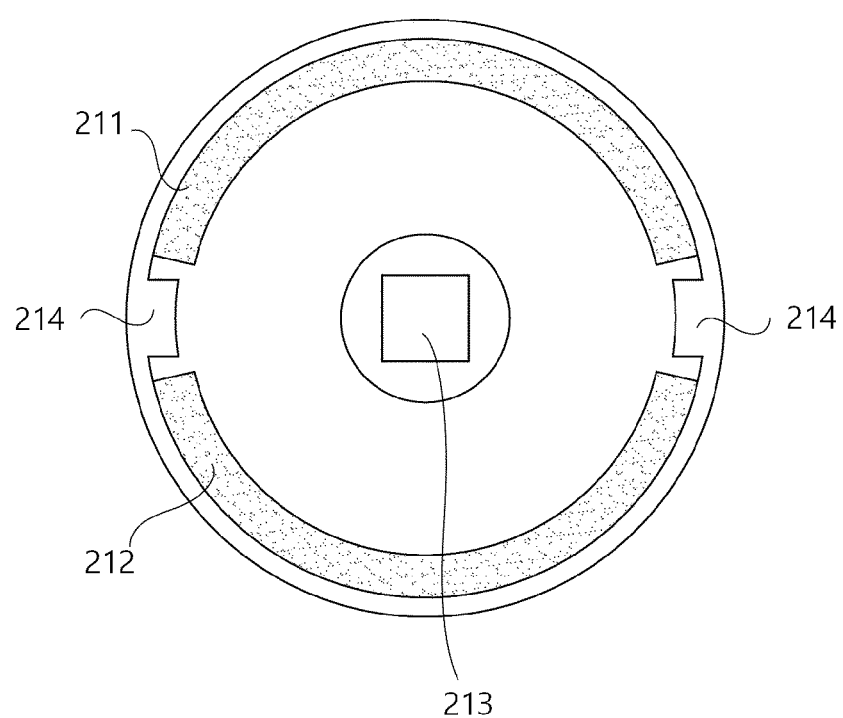
FIG. 5 is a plan view of a socket of the control board of FIG. 4.

FIG. 4 is a plan view of a control board according to an embodiment of the present invention and FIG. 5 is a plan view of a socket of the control board of FIG. 4.

Referring to FIGS. 4 and 5, the control board 200 includes a socket 210, an insertion detector 220, a controller 250, a display 260, and an audio interface 270. Further, the socket 210 includes a third electrode 211, a fourth electrode 212, and a light emitter 213.

The control board 200 includes a plurality of sockets 210 that correspond to the shape of the bottom of the to-be-detected implement 100 and in which to-be-detected implements 100 are inserted. The circumferential shape of the socket 210 corresponds to the shape of the bottom including the recessed or protruding region of the guide 140 of the to-be-detected part 150. Accordingly, when inserting a to-be-detected implement 100 into the control board 200, a user can accurately insert the to-be-detected implement 100 by fitting the bottom of the to-be-detected implement 100 and the circumferential shape of the socket 210.

At least a region of the socket 210 may be protruded or recessed toward the top or the bottom of the socket 210. When at least a region of the socket 210 is protruded or recessed toward the top or the bottom, a user can more easily insert the to-be-detected implement 100 into the control board 200.

The third electrode 211 is formed in a region of the lower portion of the socket 210. Further, the socket 210 has the fourth electrode 212 spaced apart from the third electrode 211 and formed in another region of the lower portion of the socket 210. When a user inserts the to-be-detected implement 100 into the control board 200, the first electrode 120 of the to-be-detected implement 100 is electrically connected by coming in contact with the third electrode 211 or the fourth electrode 212 of the socket 210 of the control board 200. Further, the second electrode 130 of the to-be-detected implement 100 is electrically connected by coming in contact with the third electrode 211 or the fourth electrode 212 that is not in contact with the first electrode 120.

The third electrode 211 is formed at the lower portion of the socket 210 and is configured as a conductive material exposed to the outside. The third electrode 211 may be biasedly formed in a region from protrusions 214 corresponding to the shape of the guide 140 of the to-be-detected implement 100.

The fourth electrode 212 is formed at the lower portion of the socket 210 and is configured as a conductive material exposed to the outside. The fourth electrode 212 may be biasedly formed in a region, which is different from the region in which the third electrode 211 is formed, from the protrusions 214 corresponding to the guide 140 of the to-be-detected implement 100.

The light emitter 213 is disposed to correspond to the position of each of the plurality of sockets 210 and emits light on the basis of information of the socket 210 generated by the controller 250. The light emitter 213 may emit different light in correspondence to the pattern or color of the to-be-detected implement 100 which corresponds to the value of the resistor or capacitor of the to-be-detected part 150 of each of groups of to-be-detected implements 100 to be described below.

The insertion detector 220 is connected to each of the third electrode 211 and the fourth electrode 212 and detects an electrical change due to insertion of the to-be-detected implement 100. When a user insertion the to-be-detected implement 100 into the control board 200, the insertion detector 220 detects a variation of the resistor or capacitor due to the to-be-detected part 150 of the to-be-detected implement 100. Detecting a variation of resistance and capacitance values is apparent to those skilled in the art, and detailed description of this configuration may make the spirit of the present invention, so it is not described below.

The controller 250 determines the position of the socket 210 in which the to-be-detected implement 100 is inserted on the basis of the electrical change detected by the insertion detector 220. The controller 250 determines the position of the socket 210 in which the to-be-detected implement 100 is inserted on the basis of an electrical change detected by the third electrode 211 and the fourth electrode 212 formed at the lower portion of the socket 210 in which the to-be-detected implement 100 is inserted of the plurality of sockets 210.

The controller 250 generates insertion information about the position or order of the socket 210 in which the to-be-detected implement 100 should be inserted of the plurality of sockets 210 of the control board 200 by a predetermined reference. The controller 250 generates insertion information about the position or order of the socket 210 in which the to-be-detected implement 100 should be inserted by a random or predetermined rule. The insertion information may be provided to a user by the light emitter 213, the display 260, or the audio interface 270 to be described below.

The controller 250 can control each of the components of the control board 200 on the basis of predetermined rules.

The display 260 outputs an instruction, feedback, elapsed time, a rehabilitation training result, a training grade, etc. that are provided to a user.

The audio interface 270 outputs an instruction, feedback, elapsed time, a rehabilitation training result, a training grade, etc. that are provided to a user.

A memory 280 can control data input and processed in the control board 200.

A communication unit (not shown) can transmit/receive data through wired/wireless communication with the control board 200, a server, and a user's terminal.

Figure 6:
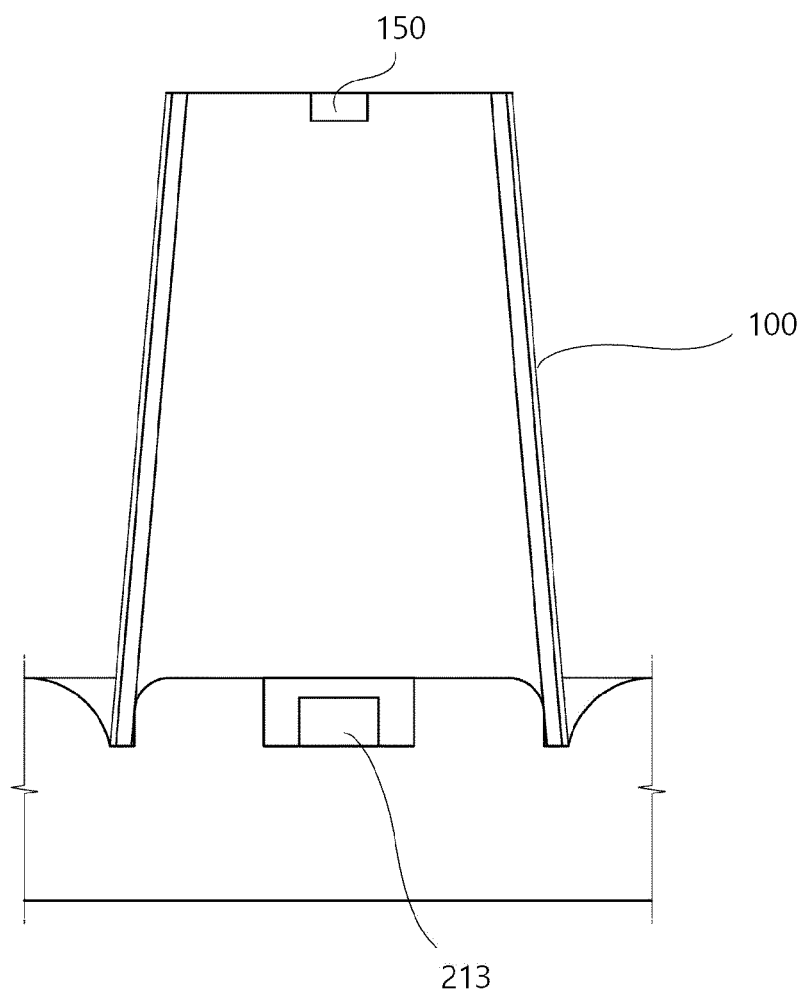
FIG. 6 is a conceptual view in which the to-be-detected implement for rehabilitation training of FIG. 2 is inserted in the control board of FIG. 4.

FIG. 6 is a conceptual view in which the to-be-detected implement for rehabilitation training of FIG. 2 is inserted in the control board of FIG. 4.

Referring to FIG. 6, the shape of the bottom of the to-be-detected implement 100 for rehabilitation training and the shape of the socket 210 of the control board 200 correspond to each other, so the to-be-detected implement 100 for rehabilitation training is inserted in the control board 200.

A user performs rehabilitation training by inserting the to-be-detected implement 100 into the socket 210. The rehabilitation training system 1000 includes to-be-detected implements 100 having various patterns or colors and can give a user an instruction to designate and insert a to-be-detected implement 100 having a specific pattern or color into the control board 200. To this end, a plurality of to-be-detected implements 100 may be provided to a user and the plurality of to-be-detected implements 100 may be classified into a plurality of groups of to-be-detected implements 100. Each of the plurality of groups of to-be-detected implements 100 may have different patterns or colors, and the values of the resistor or capacitor value of the to-be-detected parts 150 may be different from each other for each of the patterns or colors. Accordingly, when the control board 200 gives an instruction to designate and insert a to-be-detected implement 100 having a specific pattern or color into the control board 200, a user inserts the corresponding to-be-detected implement 100 into the control board 200 and the control board 200 can determine whether the to-be-detected implement 100 inserted by the user is the same as the to-be-detected implement 100 designated by the control board 200 on the basis of an electrical change detected by the to-be-detected implement 100 inserted by the user.

Figure 7:
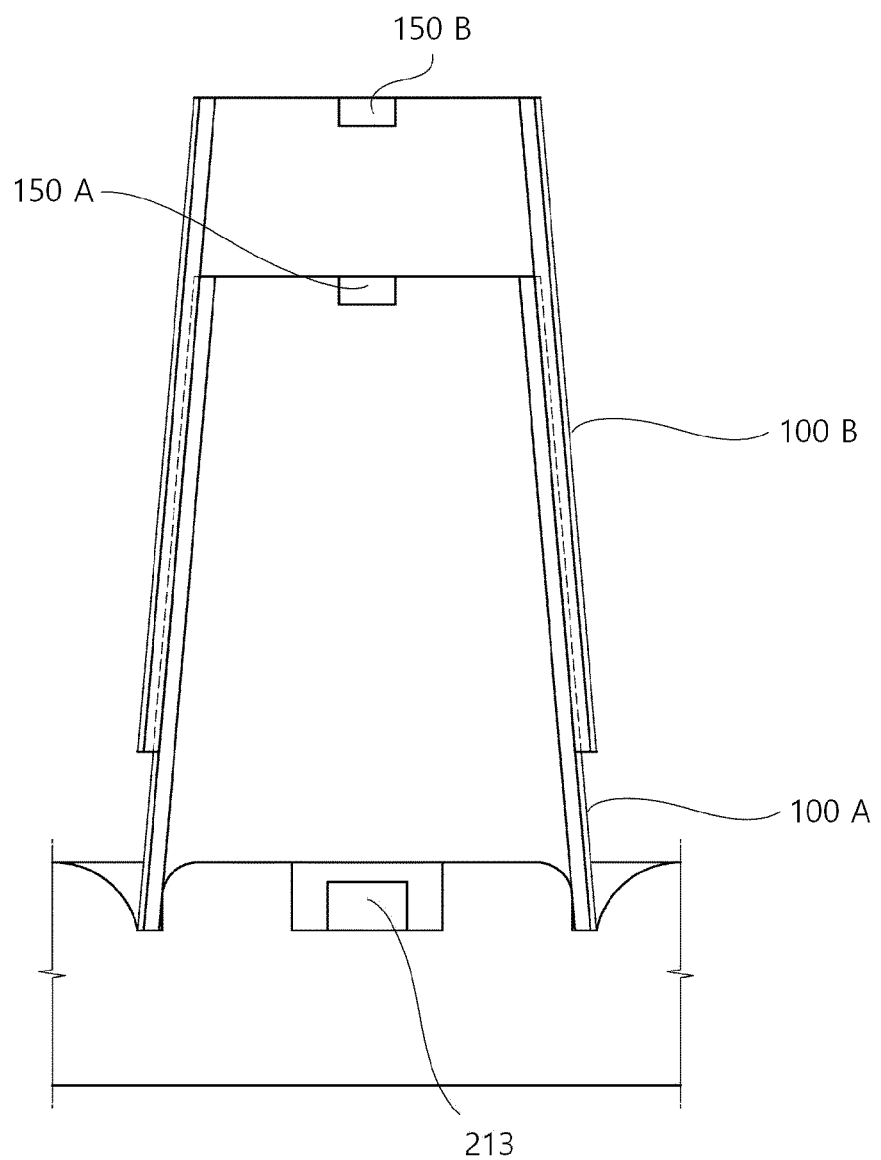
FIG. 7 is a conceptual view in which two to-be-detected implements for rehabilitation training of FIG. 2 are stacked and inserted in the control board of FIG. 4.

FIG. 7 is a conceptual view in which two to-be-detected implements for rehabilitation training of FIG. 2 are stacked and inserted in the control board of FIG. 4.

Referring to FIG. 7, another to-be-detected implement 100 B is stacked over a to-be-detected implement 100 A inserted in the control board 200.

The body 110 of the to-be-detected implement 100 may have a predetermined gradient. Two or more to-be-detected implements 100 A and 100 B of which the shapes of the bodies 110 have a predetermined gradient, as described with reference to FIG. 3, may be piled and stacked up.

With one to-be-detected implement 100 A inserted in the socket 210 of the control board 200, another to-be-detected implement 100 B is additionally stacked over the to-be-detected implement 100 A inserted in the control board 200, the guides 140 A and 140 B of the two to-be-detected implements 100 are fitted to each other, whereby the two to-be-detected implements 100 A and 100 B are electrically connected to each other.

Since the two to-be-detected implements 100 A and 100 B are electrically connected to each other, the insertion detector 220 calculates the number of the stacked to-be-detected implements 100 by detecting a change of resistors or capacitors due to the parallel connection of the resistors or the capacitors of the to-be-detected parts 150 A and 150 B. In detail, for example, when a to-be-detected implement 100 B of which the to-be-detected part 150 B has a resistance value or capacitance value A is additionally stacked with a to-be-detected implement 100 A of which the to-be-detected 150 A has a resistance value or capacitance value A inserted in the control board 200, the insertion detector 220 detects a change of the resistors or capacitors due to parallel connection of the two to-be-detected implements 100 A and 100 B of which the resistance or capacitance value is A. Further, when a to-be-detected implement 100 B of which the to-be-detected part 150 B has a resistance value or capacitance value B is additionally stacked with a to-be-detected implement 100 A of which the to-be-detected 150 A has a resistance value or capacitance value A inserted in the control board 200, the insertion detector 220 detects a change of the resistors or capacitors due to parallel connection of the two to-be-detected implements 100 A and 100 B of which the resistance or capacitance values are A and B.

The controller 250 determines the position of the socket 210 in which the to-be-detected implement 100 is additionally inserted on the basis of the change of the resistors and capacitors due to parallel connection detected by the insertion detector 220.

Figure 8:
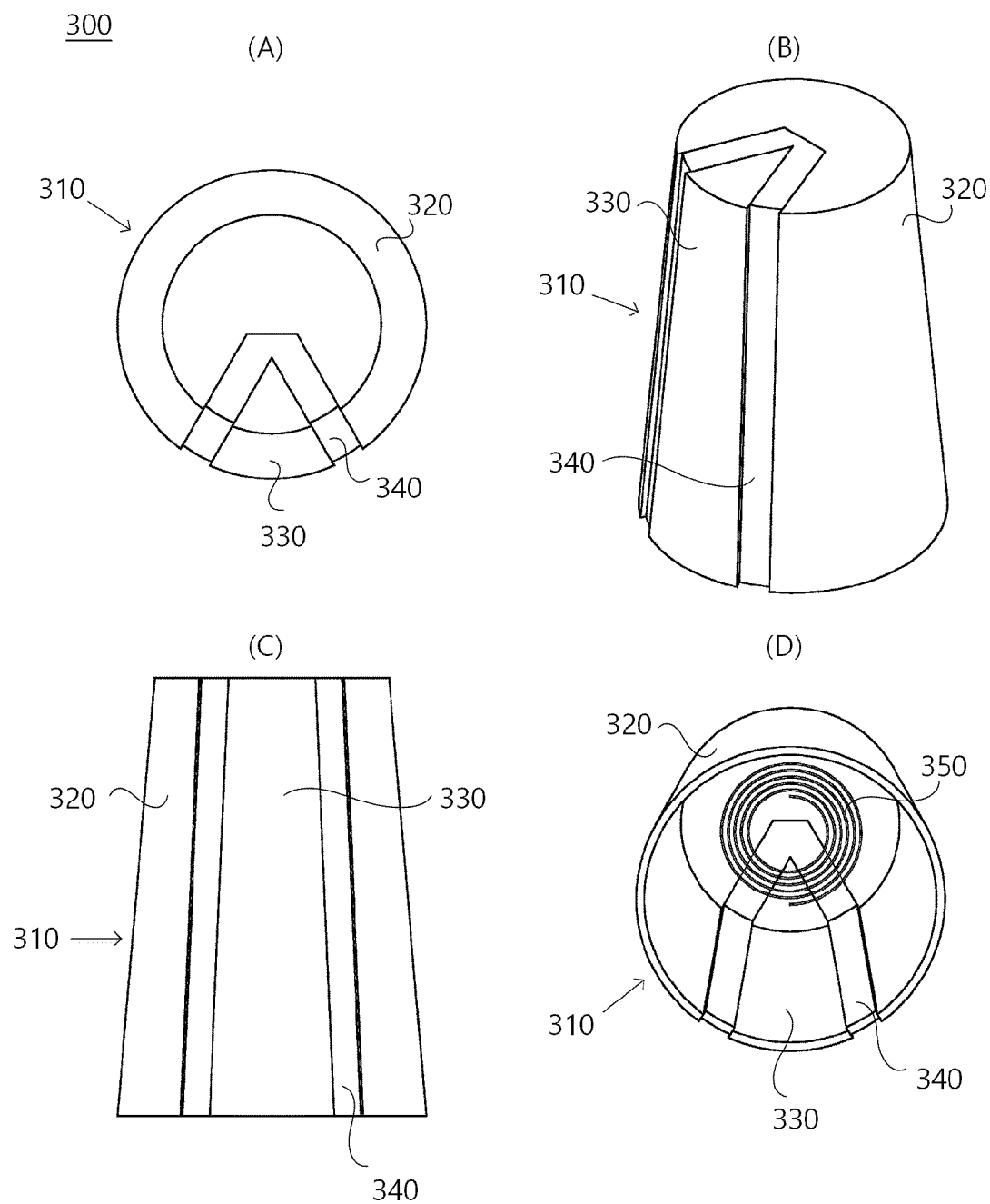
FIG. 8 is a perspective view, a plan view, and a side view of a to-be-detected implement for rehabilitation training according to another embodiment of the present invention.

FIG. 8 is a perspective view, a plan view, and a side view of a to-be-detected implement for rehabilitation training according to another embodiment of the present invention.

Referring to FIG. 8, a to-be-detected implement 300 includes a body 310, a first electrode 320, a second electrode 330, a guide 340, and a to-be-detected part 350. The top of the to-be-detected implement 300 is shown in FIG. 8A, the side of the to-be-detected implement 300 is shown in FIGS. 8B and 8C, and the bottom of the to-be-detected implement 300 is shown in FIG. 8D.

The components of the to-be-detected implement 300 for rehabilitation training of FIG. 8 partially correspond to the components of the to-be-detected implement 300 described above with reference to FIG. 2. Hereafter, in the description of the function or operation of each component of the to-be-detected implement 300 of FIG. 8, repeated description is omitted and features different from the components of the to-be-detected implement 300 of FIG. 2 are described in detail.

The body 310 of the to-be-detected implement 300 has a cylindrical shape of which at least one side is open.

The first electrode 320 of the to-be-detected implement 300 is formed in a partial region of the circumference of the body 310.

The second electrode 330 of the to-be-detected implement 300 is spaced apart from the first electrode 320 and is formed in another partial region of the circumference of the body 310.

The guide 340 of the to-be-detected implement 300 is formed between the first electrode 320 and the second electrode 330, thereby blocking electrical connection of the first electrode 320 and the second electrode 330. The guide 340 is recessed or protruded a predetermined depth on the circumference of the to-be-detected implement 300.

The to-be-detected part 350 of the to-be-detected implement 300 is in contact with the first electrode 320 on a side and the second electrode 330 on another side. The to-be-detected part 350 is configured as a first coil having a predetermined inductance value.

Unlike a resistor or a capacitor, the coil of the to-be-detected part 350 is an element having directionality. That is, the direction of an induced current may be changed in accordance with the twist direction of a coil. Accordingly, the rehabilitation training system 1000 using a coil should be designed in consideration of the direction in which the to-be-detected implement 300 is inserted in a control board 400 and the direction in which two or more to-be-detected implements 300 are stacked. In consideration of the directionality of a coil, the guide 340 of the to-be-detected implement 300 may be biased to a side of the circumference of the to-be-detected implement 300. The fact that the guide 340 of the to-be-detected implement 300 is biased to a side of the circumference of the to-be-detected implement 300 may mean that the guide 340 of the to-be-detected implement 300 is bent to a side of the circumference of the to-be-detected implement 300. Accordingly, a user inserts a to-be-detected implement 300 into the control board 400 or stacks two or more to-be-detected implements 300 in consideration of the guide 340 biased to a side, thereby being able to inserting or stacking them in a direction intended when the rehabilitation training system 1000 is designed.

Alternatively, the shape of the body 310 of the to-be-detected implement 300 may be biased to a side. For example, the shape of the bottom of the body 310 of the to-be-detected implement 300 may be a circle, the shape of the top may be a circle or an ellipse biased to a side, and the circumference of the side may be given a gradient in consideration of the shape and position of the top and the shape and position of the bottom. When the shape of the body 310 of the to-be-detected implement is biased to a side, the shape of the socket 410 of the control board 400 should also be a shape corresponding to the shape of the body 310 of the to-be-detected implement 300. That is, the shape of the socket 410 should be a shape protruding toward the top and biased to a side in correspondence to the shape of the to-be-detected implement 300. Accordingly, even though a user inserts the to-be-detected implement 300 into the control board 400 in a certain direction, it can be inserted in the direction intended when the rehabilitation training system 1000 is designed, by the shape biased to a side. Further, even though a user inserts two or more to-be-detected implements 300 in a certain direction, they can be inserted in the direction intended when the rehabilitation training system 1000 is designed, by the shape biased to a side.

In FIG. 8, the shape in which the guide 340 described above is biased to a side and the shape in which the body 310 is biased to a side may be applied in the same way to the shape of the to-be-detected implement 300 of FIG. 2.

Figure 9:
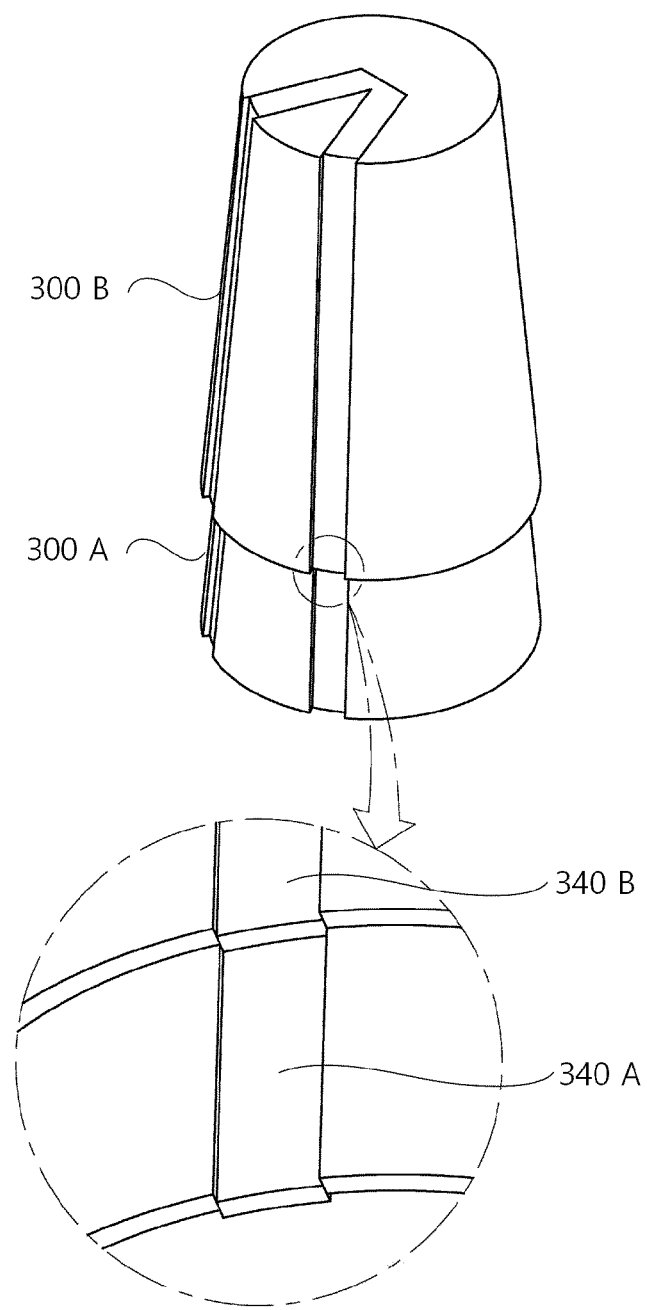
FIG. 9 is a perspective view in which to-be-detected implements for rehabilitation training of FIG. 4 are stacked.

FIG. 9 is a perspective view in which to-be-detected implements for rehabilitation training of FIG. 8 are stacked.

Referring to FIG. 9, one to-be-detected implement 300 B is stacked over another to-be-detected implement 300 A.

The body 310 of the to-be-detected implement 300 may have a predetermined gradient. Two or more to-be-detected implements 300 of which the shapes of the bodies 300 have a predetermined gradient may be piled and stacked up. When one to-be-detected 300 B is stacked over another to-be-detected implement 300 A, the guide 340 B of one to-be-detected implement 300 B is fitted in the guide 340 A of another to-be-detected implement 300 A. That is, the inner side of the recessed or protruding region of the guide 340 B of one to-be-detected implement 300 B is fitted to the outer surface of the recessed or protruding region of the guide 340 A of another to-be-detected implement 300 A.

When two or more to-be-detected implements 300 are stacked, the to-be-detected parts 350 of the two or more to-be-detected implements 300 are connected in parallel. Accordingly, when the to-be-detected part 350 is configured as a coil having a predetermined inductance value, the to-be-detected parts 350 are connected in parallel and the entire inductance value decreases when two or more to-be-detected implements 300 are stacked.

Figure 10:
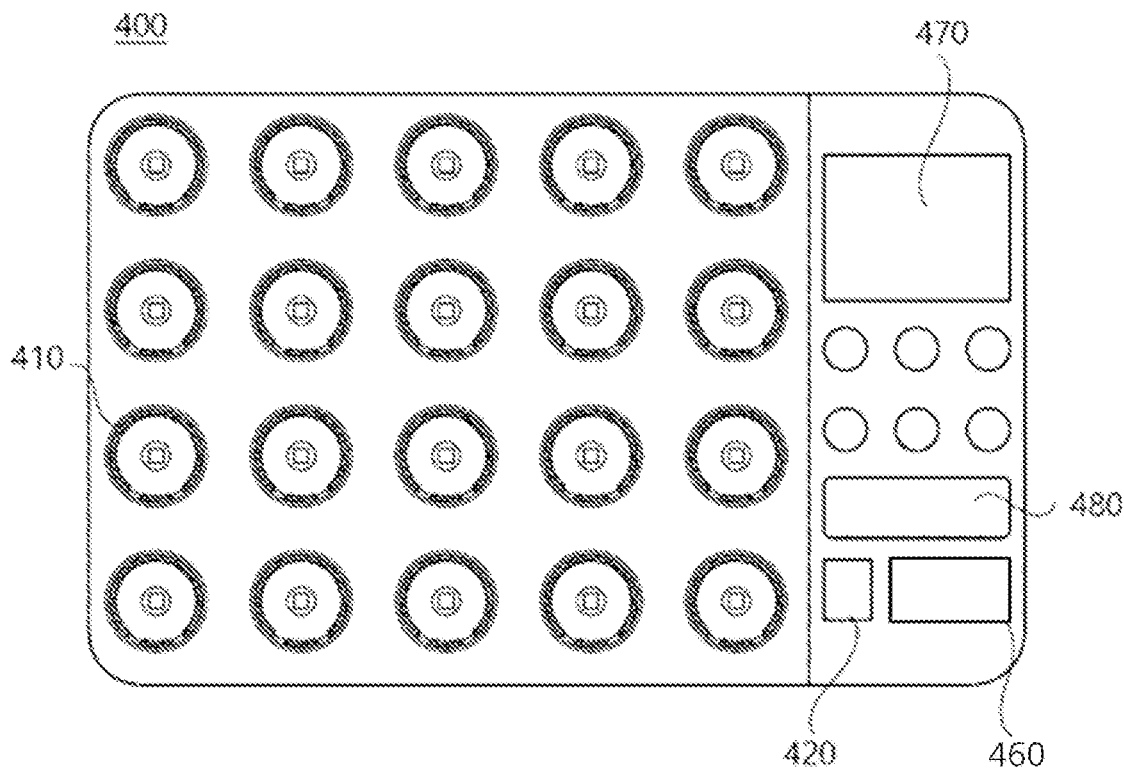
FIG. 10 is a plan view of a control board according to another embodiment of the present invention.
Figure 11:
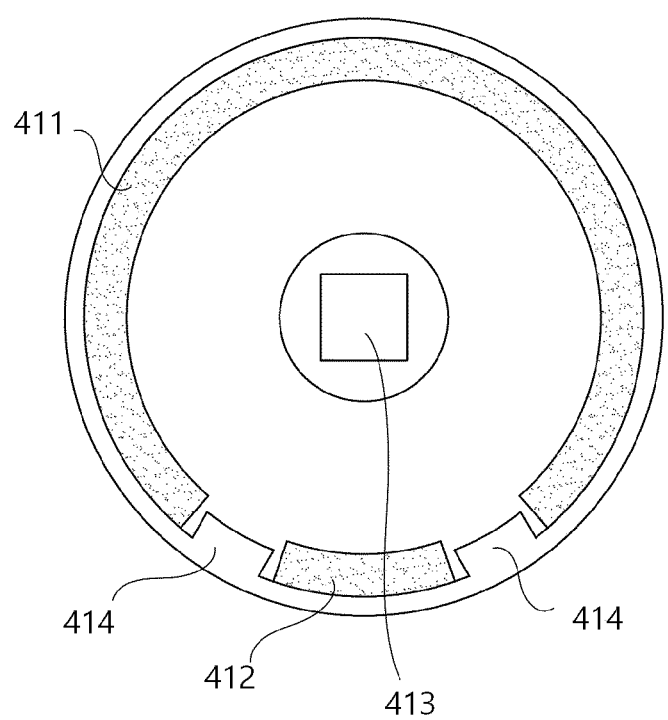
FIG. 11 is a plan view of a socket of the control board of FIG. 10.

FIG. 10 is a plan view of a control board according to another embodiment of the present invention and FIG. 11 is a plan view of a socket of the control board of FIG. 10.

Referring to FIGS. 10 and 11, the control board 400 includes a socket 410, an insertion detector 420, a controller 460, a magnetic field generator 450, a display 470, and an audio interface 480. Further, the socket 410 includes a third electrode 411, a fourth electrode 412, and a light emitter 413.

The components of the control board 400 of FIG. 10 partially correspond to the components of the control board 400 described above with reference to FIG. 4. Hereafter, in the description of the function or operation of each component of the control board 400 of FIG. 10, repeated description is omitted and features different from the components of the control board 400 of FIG. 4 are described in detail.

The control board 400 includes a plurality of sockets 410 that correspond to the shape of the bottom of the to-be-detected implement 300 and in which to-be-detected implements 300 are inserted.

The magnetic field generator 450 includes second coils disposed at the lower portion of the plurality of sockets 410, respectively, and generating a magnetic field. An induced current is generated in the first coil of the to-be-detected part 350 of the to-be-detected implement 300 by the magnetic field generated by the second coil of the magnetic field generator 450.

A plurality of magnetic field generators 450 may simultaneously generate a magnetic field. When a user inserts a to-be-detected implement 300 into one socket 410, the control board 400 can determine the position of the socket 410 in which the to-be-detected implement 300 is inserted by detecting the induced current generated at the first coil. Alternatively, one magnetic field generator 450 of a plurality of magnetic field generators 450 may generate a magnetic field in response to insertion information to be described below. When a user inserts a to-be-detected implement 300 into a socket 410 corresponding to insertion information, the control board 400 can determine insertion of the to-be-detected implement 300 or the position of the socket 410 by detecting the induced current generated at the first coil. On the other hand, when a user inserts a to-be-detected implement 300 into a socket 410 not corresponding to insertion information, the control board 400 can determine that the to-be-detected implement 300 is inserted in a socket 410 not corresponding to the insertion information.

At least a region of the socket 410 may be protruded or recessed toward the top or the bottom of the socket 410.

The third electrode 410 is formed in a region of the lower portion of the socket 411. Further, the socket 410 has the fourth electrode 412 spaced apart from the third electrode 411 and formed in another region of the lower portion of the socket 410.

The third electrode 411 is formed at the lower portion of the socket 410 and is configured as a conductive material exposed to the outside. The third electrode 411 may be biasedly formed in a region from protrusions 414 corresponding to the shape of the guide 340 of the to-be-detected implement 300.

The fourth electrode 412 is formed at the lower portion of the socket 410 and is configured as a conductive material exposed to the outside. The fourth electrode 412 may be biasedly formed in a region, which is different from the region in which the third electrode 411 is formed, from the protrusions 414 corresponding to the guide 340 of the to-be-detected implement 300.

The light emitter 413 is disposed to correspond to the position of each of the plurality of sockets 410 and emits light on the basis of insertion information generated by the controller 460. The light emitters 413 may emit different colors in correspondence to the inductance value of each of to-be-detected parts 550 in a group of to-be-detected implements 300 to be described below.

The insertion detector 420 is connected to each of the third electrode 411 and the fourth electrode 412 and detects an electrical change due to insertion of the to-be-detected implement 300. When a user insertion the to-be-detected implement 300 into the control board 400, the insertion detector 420 detects a variation of an induced current due to the to-be-detected part 350 of the to-be-detected implement 300. Detecting a variation of an induced current due to a change of an inductance value is apparent to those skilled in the art, and detailed description of this configuration may make the spirit of the present invention, so it is not described below.

The controller 460 determines the position of the socket 410 in which the to-be-detected implement 300 is inserted on the basis of the electrical change detected by the insertion detector 420.

The controller 460 generates insertion information about the position or order of the socket 410 in which the to-be-detected implement 300 should be inserted of the plurality of sockets 410 of the control board 400 by a predetermined reference.

The controller 460 can control each of the components of the control board 400 on the basis of predetermined rules.

The display 470 outputs an instruction, feedback, elapsed time, a rehabilitation training result, a training grade, etc. that are provided to a user.

The audio interface 480 outputs an instruction, feedback, elapsed time, a rehabilitation training result, a training grade, etc. that are provided to a user.

A memory 490 can control data input and processed in the control board 400.

A communication unit (not shown) can transmit/receive data through wired/wireless communication with the control board 400, a server, and a user's terminal.

Figure 12:
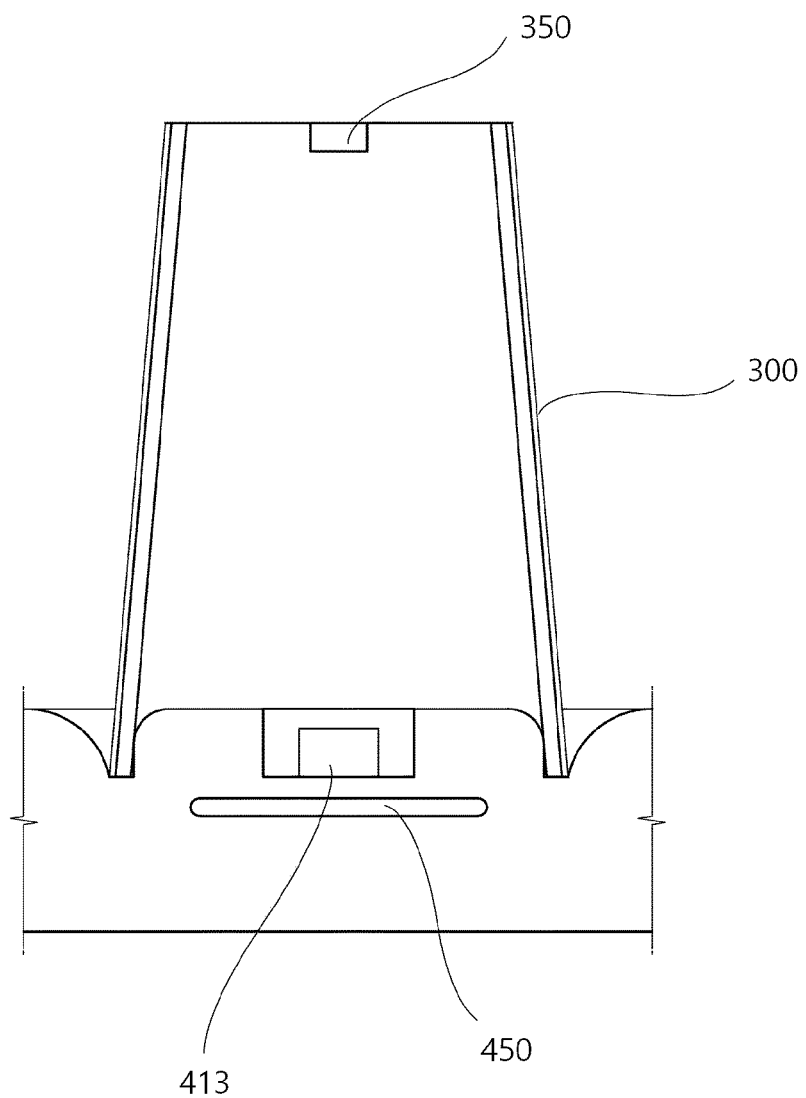
FIG. 12 is a conceptual view in which the to-be-detected implement for rehabilitation training of FIG. 8 is inserted in the control board of FIG. 10.

FIG. 12 is a conceptual view in which the to-be-detected implement for rehabilitation training of FIG. 8 is inserted in the control board of FIG. 10.

Referring to FIG. 12, the shape of the bottom of the to-be-detected implement 300 for rehabilitation training and the shape of the socket 410 of the control board 400 correspond to each other, so the to-be-detected implement 300 for rehabilitation training is inserted in the control board 400.

A user performs rehabilitation training by inserting the to-be-detected implement 300 into the socket 410. The rehabilitation training system 1000 includes to-be-detected implements 300 having various patterns or colors and can give a user an instruction to designate and insert a to-be-detected implement 300 having a specific pattern or color into the control board 400. To this end, a plurality of to-be-detected implements 300 may be provided to a user and the plurality of to-be-detected implements 300 may be classified into a plurality of groups of to-be-detected implements 300. Each of the plurality of groups of to-be-detected implements 300 may have different patterns or colors, and the inductance value of the first coil of the to-be-detected parts 350 may be different from each other for each of the patterns or colors. Accordingly, when the control board 400 gives an instruction to designate and insert a to-be-detected implement 300 having a specific pattern or color into the control board 400, a user can insert the corresponding to-be-detected implement 300 into the control board 400. The control board 400 can determine whether the to-be-detected implement 300 inserted by the user and the to-be-detected implement 300 designated by the control board 400 are the same on the basis of the electrical change detected by the to-be-detected implement 300 inserted by the user.

Figure 13:
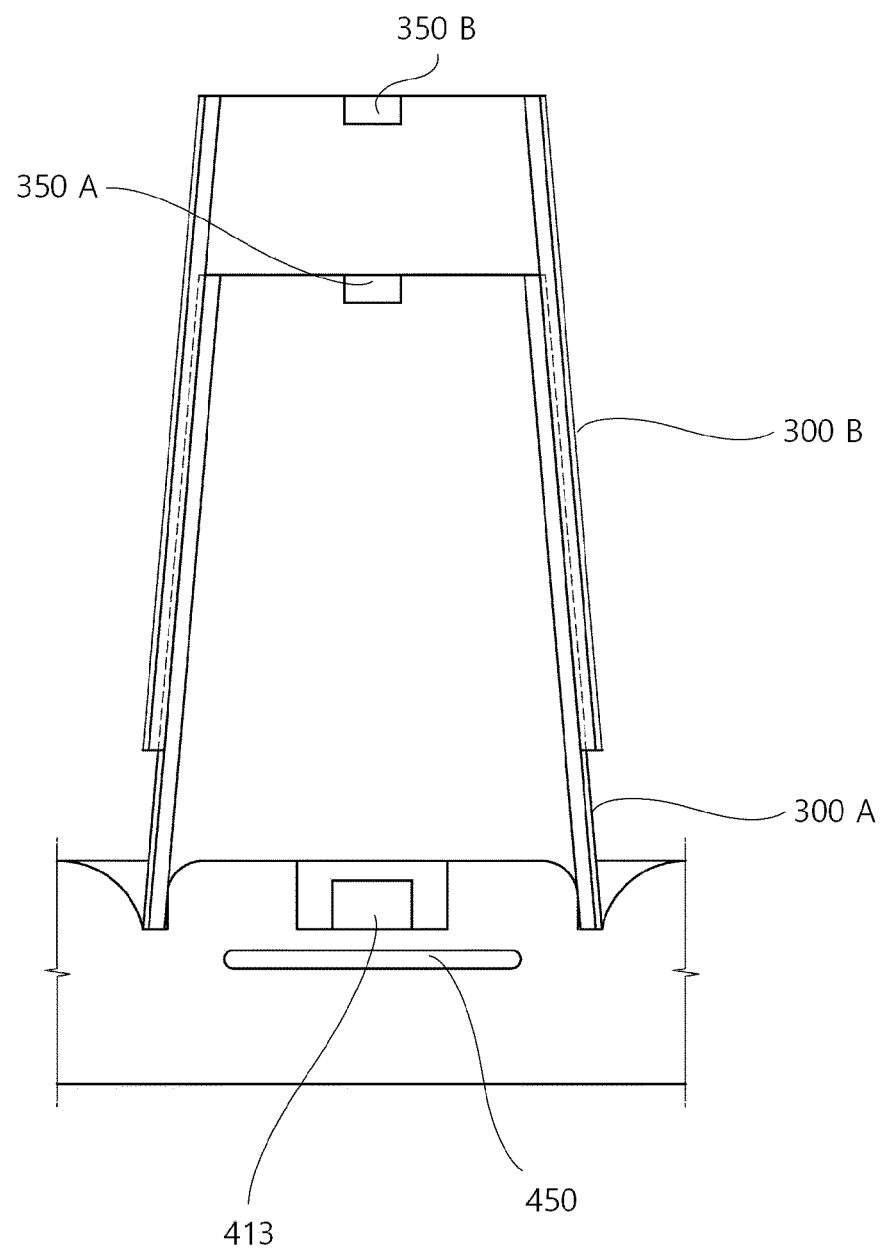
FIG. 13 is a conceptual view in which two to-be-detected implements for rehabilitation training of FIG. 8 are stacked and inserted in the control board of FIG. 10.

FIG. 13 is a conceptual view in which two to-be-detected implements for rehabilitation training of FIG. 8 are stacked and inserted in the control board of FIG. 10.

Referring to FIG. 13, another to-be-detected implement 300 B is stacked over a to-be-detected implement 300 A inserted in the control board 400.

The body 310 of the to-be-detected implement 300 may have a predetermined gradient. Two or more to-be-detected implements 300 A and 300 B of which the shapes of the bodies 310 have a predetermined gradient, as described with reference to FIG. 9, may be piled and stacked up.

With one to-be-detected implement 300 A inserted in the socket 410 of the control board 400, another to-be-detected implement 300 B is additionally stacked over the to-be-detected implement 300 A inserted in the control board 400, the guides 340 A and 340 B of the two to-be-detected implements 300 A and 300 B are fitted to each other, whereby the two to-be-detected implements 300 A and 300 B are electrically connected to each other.

Since the two to-be-detected implements 300 A and 300 B are electrically connected to each other, the insertion detector 420 calculates the number of the stacked to-be-detected implements 300 by detecting a change of an induced current due to parallel connection of the first coils of the to-be-detected parts 350 A and 350 B. In detail, for example, when a to-be-detected implement 300 B of which the to-be-detected part 350 B has an inductance value A is additionally stacked with a to-be-detected implement 300 A of which the to-be-detected 350 A has an inductance value A inserted in the control board 400, the insertion detector 420 detects a change of an induced current due to parallel connection of the two to-be-detected implements 300 A and 300 B of which the inductance value is A. Further, when a to-be-detected implement 300 B of which the to-be-detected part 350 B has an inductance value B is additionally stacked with a to-be-detected implement 300 A of which the to-be-detected 350 A has an inductance value A inserted in the control board 400, the insertion detector 420 detects a change of an induced current due to parallel connection of the two to-be-detected implements 300 A and 300 B of which the inductance values are A and B.

The controller 460 determines the position of the socket 410 in which the to-be-detected implement 300 is additionally inserted on the basis of the change of the induced current due to parallel connection detected by the insertion detector 420.

Figure 14:
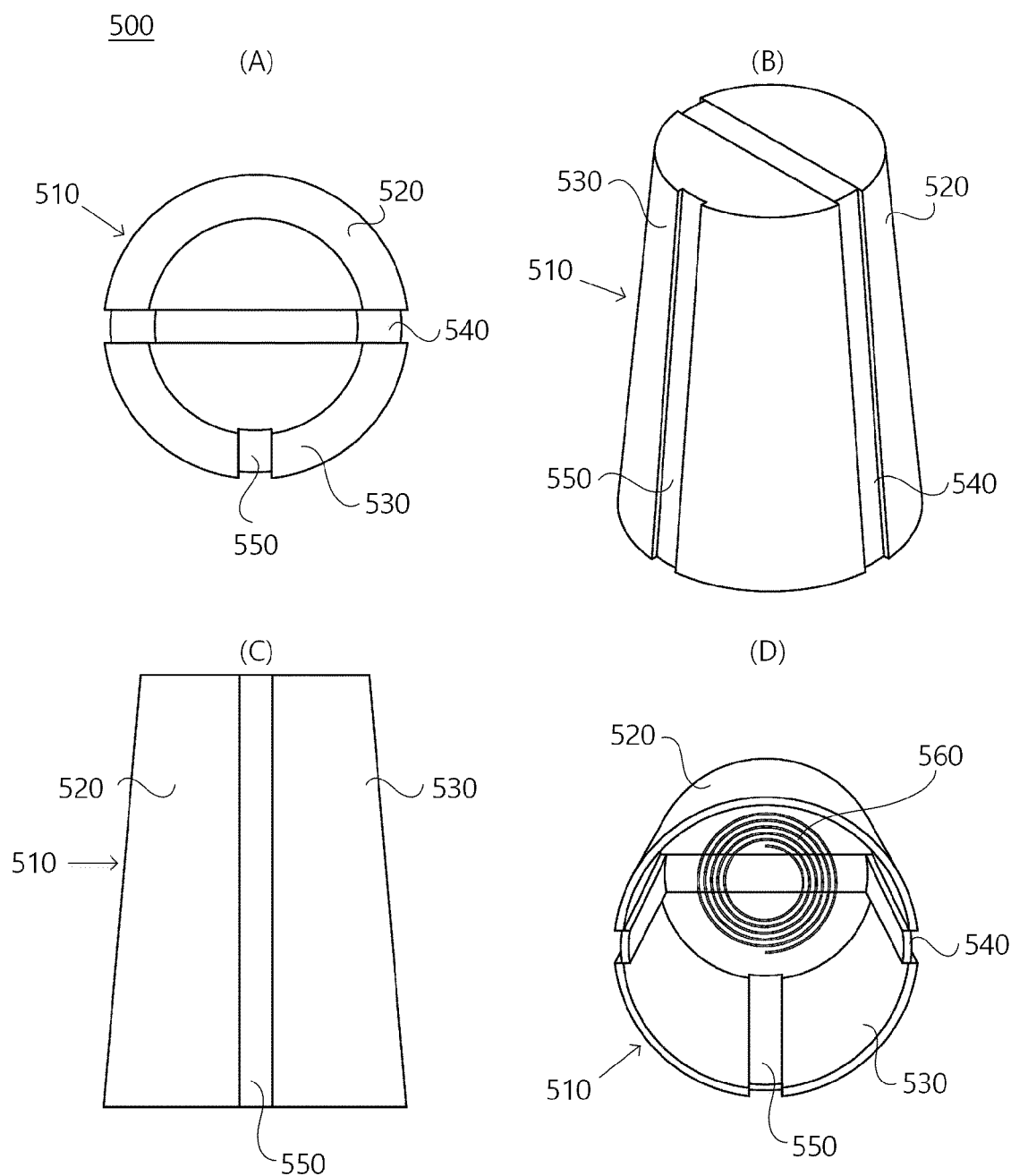
FIG. 14 is a perspective view, a plan view, and a side view of a to-be-detected implement for rehabilitation training according to another embodiment of the present invention.

FIG. 14 is a perspective view, a plan view, and a side view of a to-be-detected implement for rehabilitation training according to another embodiment of the present invention.

Referring to FIG. 14, a to-be-detected implement 500 includes a body 510, a first electrode 520, a second electrode 530, a first guide 540, a second guide 550, and a to-be-detected part 560. The top of the to-be-detected implement 500 is shown in FIG. 14A, the side of the to-be-detected implement 500 is shown in FIGS. 14B and 14C, and the bottom of the to-be-detected implement 500 is shown in FIG. 14D.

The components of the to-be-detected implement 500 of FIG. 14 partially correspond to the components of the to-be-detected implement 500 described above with reference to FIG. 8. For reference, the first guide 540 of FIG. 14 corresponds to the function or operation of the guide of FIG. 2. Further, the first guide 540 of FIG. 14 has a shape not biased to a side. Hereafter, in the description of the function or operation of each component of the to-be-detected implement 500 of FIG. 14, repeated description is omitted and features different from the components of the to-be-detected implement 500 of FIG. 8 are described in detail.

The second guide 550 of the to-be-detected implement 500 is recessed or protruded on the first electrode 520 or the second electrode 530. The first coil of the to-be-detected part 560 of the to-be-detected implement 550 has directionality the same as that described above with reference to FIG. 8. Accordingly, when the to-be-detected implement 500 is inserted in the control board 600 or two or more to-be-detected implements 500 are stacked, the inserting or stacking direction may be determined by the second guide 550.

The second guide 550 described with reference to FIG. 14 may be additionally applied in the same way to the shape of the to-be-detected implement 500 of FIG. 2.

Figure 15:
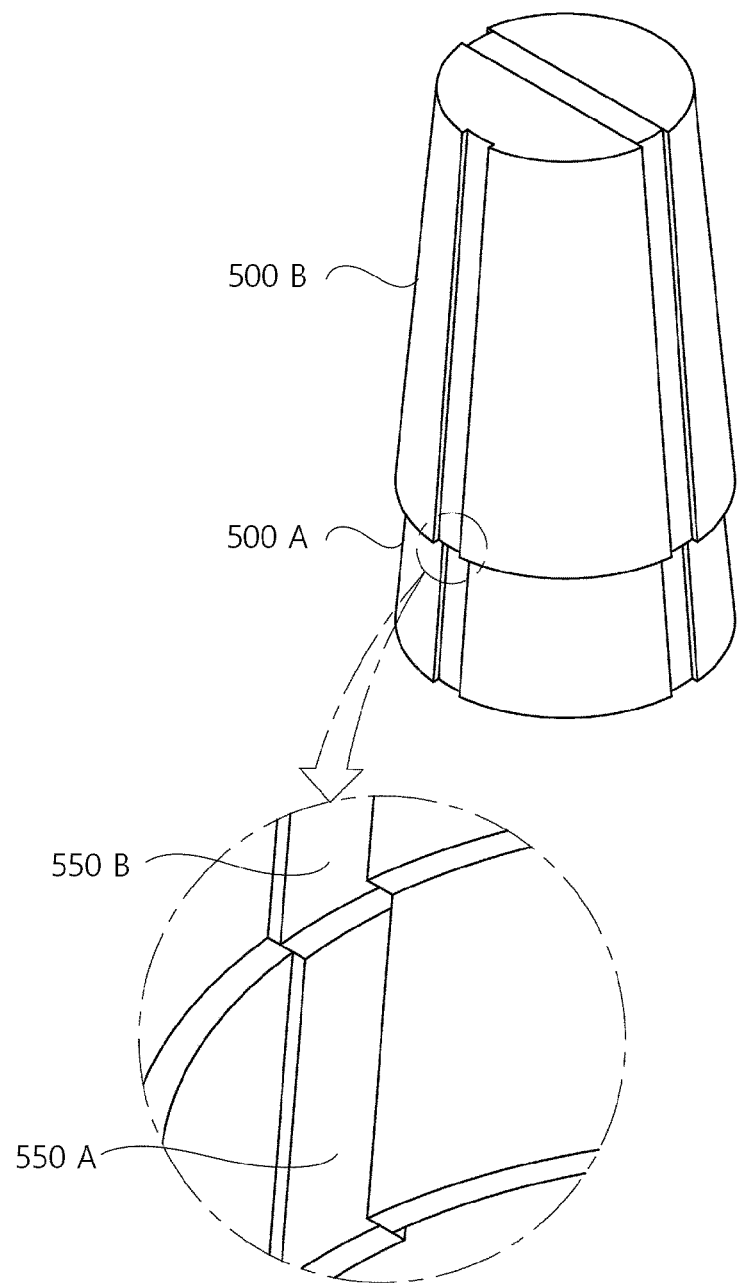
FIG. 15 is a perspective view in which to-be-detected implements for rehabilitation training of FIG. 14 are stacked.

FIG. 15 is a perspective view in which to-be-detected implements for rehabilitation training of FIG. 14 are stacked.

Referring to FIG. 15, one to-be-detected implement 500 B is stacked over another to-be-detected implement 500 A.

Since the guides 550 A and 50 B of two or more to-be-detected implements 500 A and 500 B are fitted and stacked over each other, the two or more to-be-detected implements 500 A and 500 B may be stacked with the same directionality.

Figure 16:
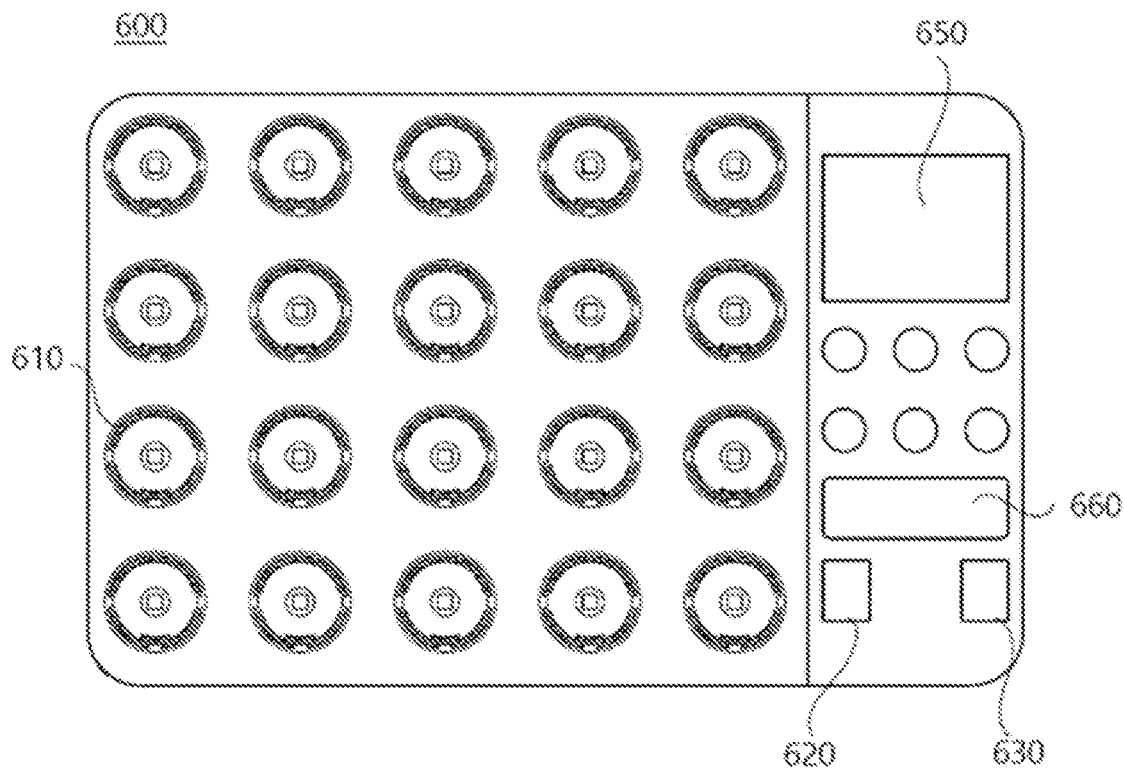
FIG. 16 is a plan view of a control board according to another embodiment of the present invention.
Figure 17:
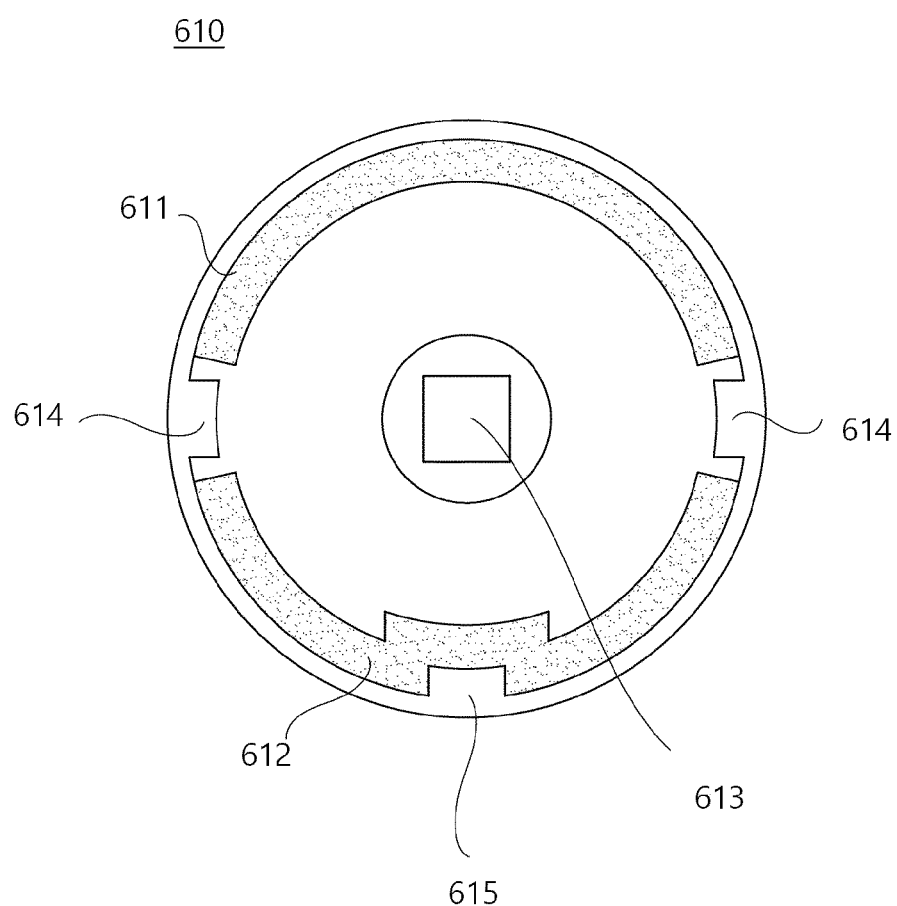
FIG. 17 is a plan view of a socket of the control board of FIG. 16.

FIG. 16 is a plan view of a control board according to another embodiment of the present invention and FIG. 17 is a plan view of a socket of the control board of FIG. 16.

Referring to FIGS. 16 and 17, a control board 600 includes a magnetic field generator 670, a socket 610, an insertion detector 620, a controller 630, a display 650, and an audio interface 660. Further, the socket 610 includes a third electrode 611, a fourth electrode 612, and a light emitter 613.

The components of the control board 600 of FIG. 16 correspond to the components of the control board 600 described above with reference to FIG. 10. Hereafter, the function or operation of each component of the to-be-detected implement 500 is not described.

The components of the socket 610 of FIG. 17 partially correspond to the components of the socket 610 described above with reference to FIG. 11. Hereafter, in the description of the function or operation of each component of the socket 610 of FIG. 17, repeated description is omitted and features different from the components of the socket 610 of FIG. 11 are described in detail.

The insertion unit 610 includes a first protrusion 614 and a second protrusion 615. The first protrusion 614 corresponds to the shape of the first guide 540 of the to-be-detected implement 500. On the other hand, the second protrusion 615 corresponds to the shape of the second guide of the to-be-detected implement 500. A user checks the positions of the second guide 550 of the to-be-detected implement 500 and the second protrusion 615 of the socket 610, and inserts the to-be-detected implement 500 into the socket 610.

Figure 18:
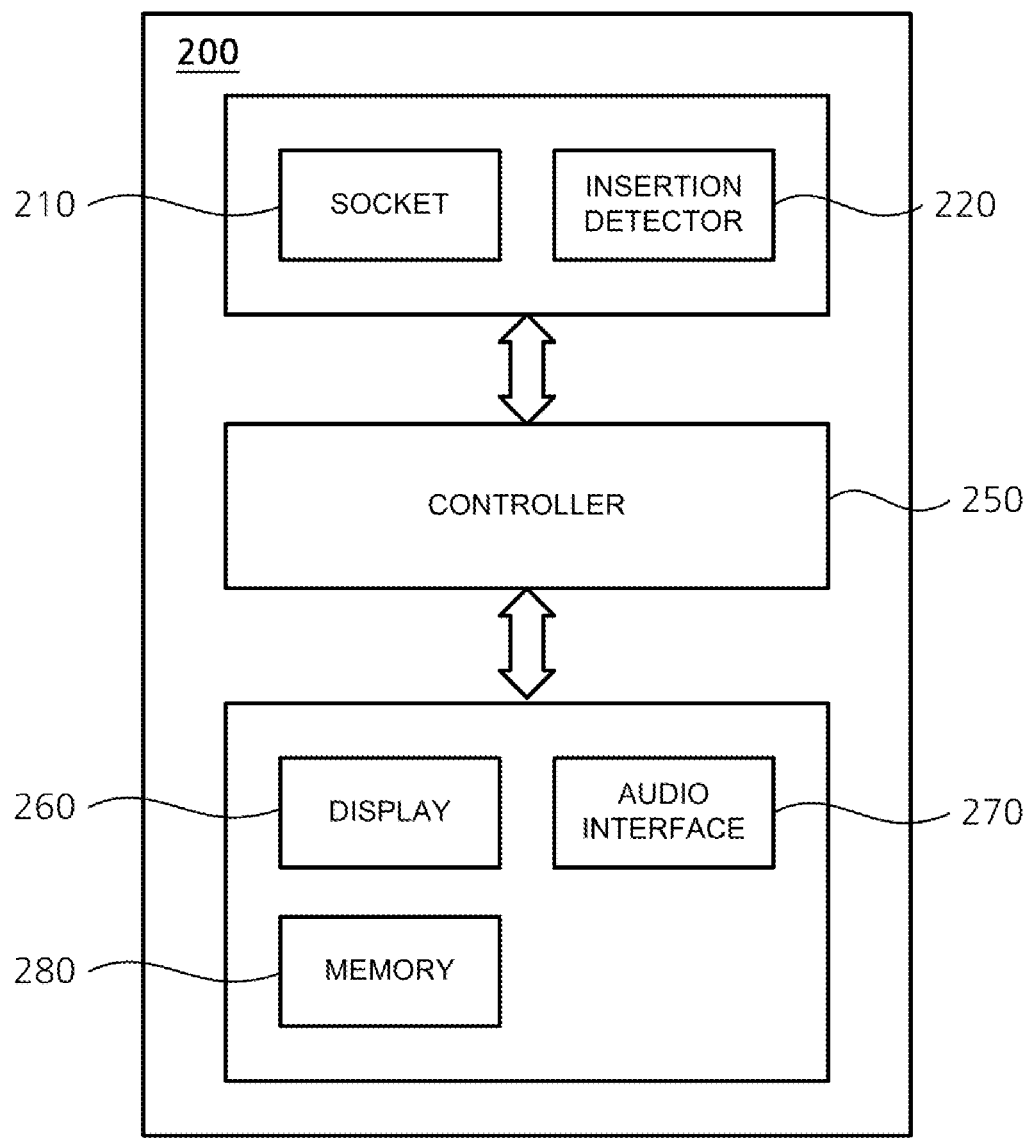
FIG. 18 is a schematic block diagram of the to-be-detected implement of FIG. 2 and the control board of FIG. 4.

FIG. 18 is a schematic block diagram of the control board of FIG. 4.

Referring to FIG. 18, the control board 200 includes a socket 210, an insertion detector 220, a controller 250, a display 260, an audio interface 270, a memory 280, and a communication unit (not shown).

The control board 200 of FIG. 18 corresponds to the function or operation of the control board 200 described above with reference to FIGS. 2 to 7.

Figure 19:
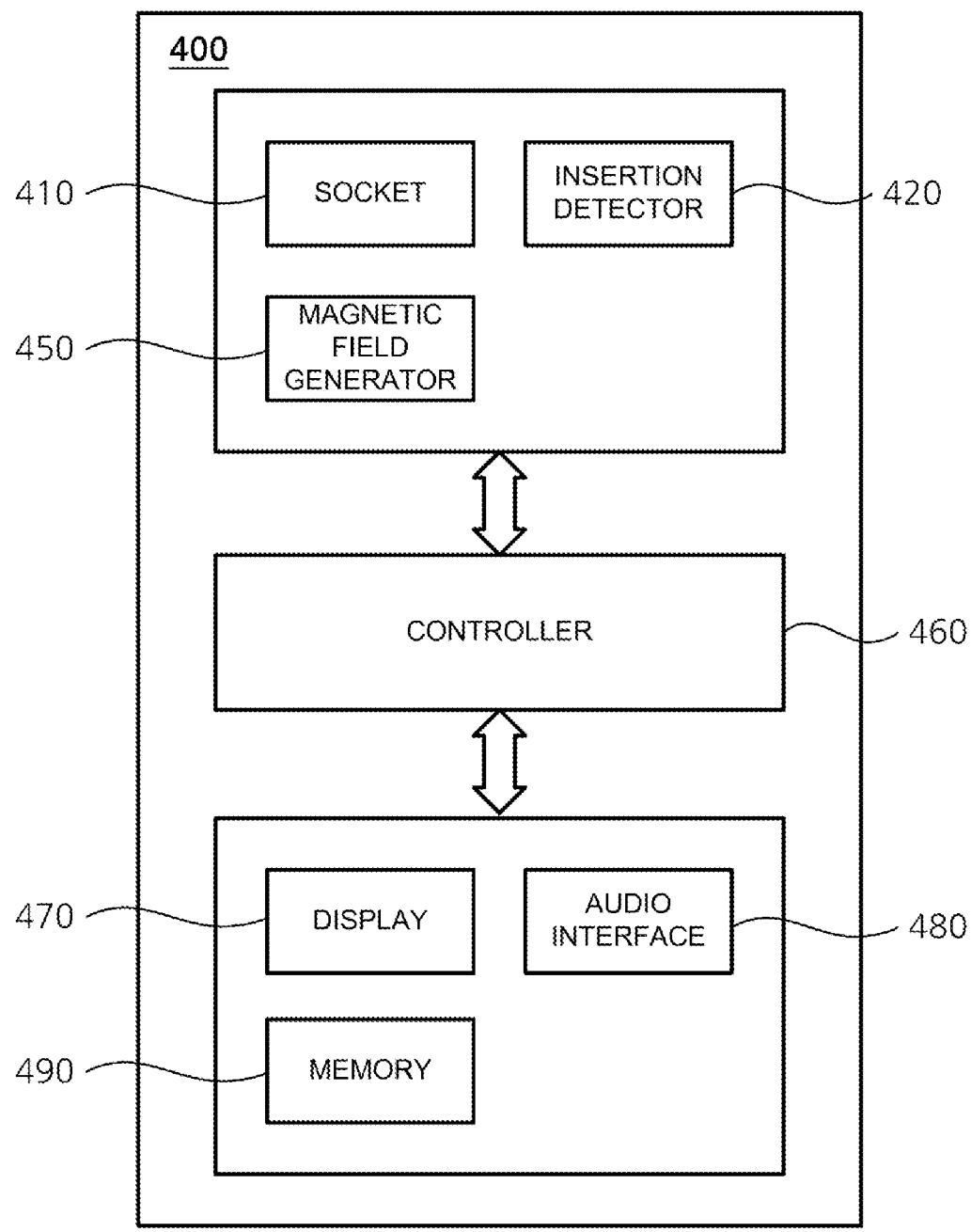
FIG. 19 is a schematic block diagram of the to-be-detected implement of FIG. 8 and the control board of FIG. 10.

FIG. 19 is a schematic block diagram of the control board of FIG. 10.

Referring to FIG. 19, the control board 400 includes a socket 410, an insertion detector 420, a magnetic field generator 450, a controller 460, a display 470, an audio interface 480, a memory 490, and a communication unit (not shown).

The control board 400 of FIG. 19 corresponds to the function or operation of the control board 400 described above with reference to FIGS. 8 to 13.

The steps of the method or algorithm described in relation to embodiments of the present invention may be directly implemented by hardware, may be implemented by a software module that is executed by hardware, or may be implemented by a combination thereof. As software module may be permanently stationed on a RAM (Random Access Memory), a ROM (Read Only Memory), an EPROM (Erasable Programmable ROM), an EEPROM (Electrically Erasable Programmable ROM), a flash memory, a hard disk, a detachable disk, a CD-ROM, or a certain type of computer-readable recording medium well known in the art.

Although an exemplary embodiment of the present invention was described above with reference to the accompanying drawings, those skilled in the art would understand that the present invention may be implemented in various ways without changing the necessary features or the spirit of the prevent invention. Therefore, the embodiments described above are only examples and should not be construed as being limitative in all respects.

The invention claimed is:

1. A to-be-detected implement for rehabilitation training, comprising:
    a first body; and a second body,
wherein the first body and the second body have the same truncated cone shape,
wherein each of the first body and the second body comprises:
a first electrode that configures a first part of a side wall of a respective body, a first part of a top plate of the respective body, and a first part of an opened bottom surface of the respective body;
a second electrode that configures a second part of the side wall of the respective body, a second part of the top plate of the respective body, and a second part of the opened bottom surface of the respective body;
a guide positioned between the first electrode and the second electrode, and separating the first electrode and the second electrode, wherein the guide is recessed a predetermined depth from an outer surface of the first electrode and an outer surface of the second electrode, and protruded the predetermined depth from an inner surface of the first electrode and an inner surface of the second electrode;
a to-be-detected part positioned on a center portion of an inner surface of the top plate of the respective body, and connecting the first electrode and the second electrode, and
wherein an outer surface of the guide of the first body is configured to accommodate an inner surface of the guide of the second body when the second body is stacked over the first body.

2. The to-be-detected implement of claim 1, wherein the to-be-detected part is configured as a resistor having a predetermined resistance value or a capacitor having a predetermined capacitance value.

3. The to-be-detected implement of claim 1, wherein the guide has a shape of an angled line that traverses between the first electrode and the second electrode.

4. The to-be-detected implement of claim 1, wherein the to-be-detected part of the respective body comprises a first coil having a predetermined inductance value.

5. The to-be-detected implement of claim 1, wherein each of the first body and the second body further comprises an additional guide formed on the first electrode, separately from the guide positioned between the first electrode and the second electrode.

6. A rehabilitation training system comprising:
a to-be-detected implement for rehabilitation training; and
a control board,
wherein the to-be-detected implement for rehabilitation training comprises:
a first body; and
a second body,
wherein the first body and the second body have the same truncated cone shape,
wherein each of the first body and the second body comprises:
a first electrode that configures a first part of a side wall of a respective body, a first part of a top plate of the respective body, and a first part of an opened bottom surface of the respective body;
a second electrode that configures a second part of the side wall of the respective body, a second part of the top plate of the respective body, and a second part of the opened bottom surface of the respective body;
a guide positioned between the first electrode and the second electrode, and separating the first electrode and the second electrode, wherein the guide is recessed a predetermined depth from an outer surface of the first electrode and an outer surface of the second electrode, and protruded the predetermined depth from an inner surface of the first electrode and an inner surface of the second electrode; and
a to-be-detected part positioned on a center portion of an inner surface of the top plate of the respective body, and connecting the first electrode and the second electrode,
wherein an outer surface of the guide of the first body is configured to accommodate an inner surface of the guide of the second body when the second body is stacked over the first body,
wherein the control board comprises a plurality of sockets, wherein each socket of the plurality of sockets has a shape corresponding to the opened bottom surface of the respective body, and the respective body is configured to be inserted into one of the plurality of sockets
wherein each socket of the plurality of sockets comprises:
a third electrode formed in a region of a lower portion of a respective socket; and
a fourth electrode spaced apart from the third electrode and formed in another region of the lower portion of the respective socket, and
wherein the control board is configured to:
detect an electrical change due to an insertion of the respective body to one of the plurality of sockets; and
determine a position of the respective socket in which the respective body is inserted, based on the detected electrical change.

7. The rehabilitation training system of claim 6, wherein when the second body is stacked over the first body, the control board is further configured to calculate a number of stacked bodies by detecting a change due to parallel connection of resistors or capacitors of the to-be-detected parts of the stacked bodies, and the control board is further configured to determine the position of the respective socket in which the stacked bodies are inserted, based on a change of resistors or capacitors due to the parallel connection of the stacked bodies.

8. The rehabilitation training system of claim 6, wherein the to-be-detected part of the first body and the to-be-detected part of the second body have different values of resistors or capacitors.

9. The rehabilitation training system of claim 6, wherein the control board is further configured to generate insertion information of the position of the respective socket, in which the respective body is to be inserted.

10. The rehabilitation training system of claim 9, wherein the respective socket comprises a light emitter configured to emit light based on the insertion information.

11. A rehabilitation training system comprising:
a to-be-detected implement for rehabilitation training; and
a control board,
wherein the to-be-detected implement for rehabilitation training comprises:
a first body; and
a second body,
wherein the first body and the second body have the same truncated cone shape,
wherein each of the first body and the second body comprises:
a first electrode that configures a first part of a side wall of a respective body, a first part of a top plate of the respective body, and a first part of an opened bottom surface of the respective body;

a second electrode that configures a second part of the side wall of the respective body, a second part of the top plate of the respective body, and a second part of the opened bottom surface of the respective body;

a guide positioned between the first electrode and the second electrode, and separating the first electrode and the second electrode, wherein the guide is recessed a predetermined depth from an outer surface of the first electrode and an outer surface of the second electrode, and protruded the predetermined depth from an inner surface of the first electrode and an inner surface of the second electrode; and a to-be-detected part positioned on a center portion of an inner surface of the top plate of the respective body, and connecting the first electrode and the second electrode, wherein an outer surface of the guide of the first body is configured to accommodate an inner surface of the guide of the second body when the second body is stacked over the first body, wherein the control board comprises a plurality of sockets, wherein each socket of the plurality of sockets has a shape corresponding to the opened bottom surface of the respective body, and the respective body is configured to be inserted into one of the plurality of sockets, wherein each socket of the plurality of sockets comprises:

a third electrode formed in a region of a lower portion of a respective socket; and a fourth electrode spaced apart from the third electrode and formed in another region of the lower portion of the respective socket, and wherein the control board further comprises:

a magnetic field generator disposed at the lower portion of the respective socket; and wherein the control board is configured to:

detect an electrical change due to an insertion of the respective body to one of the plurality of sockets; and determine a position of the respective socket in which the respective body is inserted, based on the detected electrical change.

12. The rehabilitation training system of claim 11, wherein when the second body is stacked over the first body, the control board is further configured to calculate a number of stacked bodies by detecting a change of an induced current due to a parallel connection of first coils of the to-be-detected parts of the stacked bodies, and the control board is further configured to determine the position of the respective socket in which the stacked bodies are inserted, based on a change of an induced current due to the parallel connection.

13. The rehabilitation training system of claim 11, wherein an inductance value of a first coil of the first body is different from an inductance value of a first coil of the second body.

14. The rehabilitation training system of claim 11, wherein the control board is further configured to generate insertion information of the position of the respective socket, in which the respective body is to be inserted.

15. The rehabilitation training system of claim 14, wherein the respective socket comprises a light emitter configured to emit light based on the insertion information.

* * * * *